(12) United States Patent
Nichols et al.

(10) Patent No.: US 9,187,567 B2
(45) Date of Patent: Nov. 17, 2015

(54) ASSAY TO DETERMINE LRRK2 ACTIVITY IN PARKINSON'S DISEASE

(75) Inventors: Jeremy Nichols, Sunnyvale, CA (US); Birgitt Schüle, Sunnyvale, CA (US)

(73) Assignee: PARKINSON'S INSTITUTE, Sunnyvale, CA (US)

( * ) Notice: Subject to any disclaimer, the term of this patent is extended or adjusted under 35 U.S.C. 154(b) by 0 days.

(21) Appl. No.: 14/118,547

(22) PCT Filed: May 18, 2012

(86) PCT No.: PCT/US2012/038696
§ 371 (c)(1),
(2), (4) Date: Feb. 6, 2014

(87) PCT Pub. No.: WO2012/159079
PCT Pub. Date: Nov. 22, 2012

(65) Prior Publication Data
US 2014/0141451 A1  May 22, 2014

Related U.S. Application Data

(60) Provisional application No. 61/487,639, filed on May 18, 2011, provisional application No. 61/487,628, filed on May 18, 2011, provisional application No. 61/537,463, filed on Sep. 21, 2011.

(51) Int. Cl.
| C07K 16/44 | (2006.01) |
| G01N 33/573 | (2006.01) |
| C07K 16/40 | (2006.01) |
| G01N 33/577 | (2006.01) |
| G01N 33/68 | (2006.01) |

(52) U.S. Cl.
CPC ............... *C07K 16/40* (2013.01); *C07K 16/44* (2013.01); *G01N 33/573* (2013.01); *G01N 33/577* (2013.01); *G01N 33/6896* (2013.01); *G01N 2800/2835* (2013.01)

(58) Field of Classification Search
None
See application file for complete search history.

(56) References Cited

U.S. PATENT DOCUMENTS

| 4,474,893 A | 10/1984 | Reading |
| 4,676,980 A | 6/1987 | Segal et al. |
| 4,816,567 A | 3/1989 | Cabilly et al. |
| 5,120,644 A | 6/1992 | Ikenaka et al. |
| 5,141,852 A | 8/1992 | Egan et al. |
| 5,846,739 A | 12/1998 | Gould et al. |
| 5,989,838 A | 11/1999 | Zavada et al. |
| 2007/0218528 A1 | 9/2007 | Miller |
| 2008/0090238 A1 | 4/2008 | Yang et al. |
| 2009/0004112 A1 | 1/2009 | Abeliovich |
| 2009/0117617 A1 | 5/2009 | Holmes et al. |
| 2009/0324559 A1 | 12/2009 | Sakurada et al. |
| 2010/0003757 A1 | 1/2010 | Mack et al. |
| 2010/0041054 A1 | 2/2010 | Mack |
| 2010/0047805 A1 | 2/2010 | Wang |
| 2010/0055793 A1 | 3/2010 | Chandrasegaran |
| 2010/0068742 A1 | 3/2010 | Alessi et al. |
| 2010/0167286 A1 | 7/2010 | Reijo Pera et al. |
| 2010/0273769 A1 | 10/2010 | Roder |
| 2011/0086015 A1 | 4/2011 | Mccray et al. |

FOREIGN PATENT DOCUMENTS

| WO | WO 93/10461 A1 | 5/1993 |
| WO | WO 2010/031988 A2 | 3/2010 |
| WO | WO 2011/131980 A1 | 10/2011 |

OTHER PUBLICATIONS

Baba, et al. Aggregation of alpha-synuclein in Lewy bodies of sporadic Parkinson's disease and dementia with Lewy bodies. Am J Pathol. Apr. 1998; 152(4):879-84.
Blow, N. Antibodies: The generation game. Nature. Jun. 7, 2007; 447(7145):741-4.
Chow, et al. Measurement of MAP kinase activation by flow cytometry using phospho-specific antibodies to MEK and ERK: potential for pharmacodynamic monitoring of signal transduction inhibitors. Cytometry. Apr. 15, 2001; 46(2):72-8.
Cote, et al. Generation of human monoclonal antibodies reactive with cellular antigens. Proc Natl Acad Sci U S A. Apr. 1983;80(7):2026-30.
Czernik, et al. Phosphorylation State-Specific Antibodies. Regulatory Protein Modification Neuromethods vol. 30, 1997, pp. 219-250.
Czernik, et al. Phosphorylation state-specific antibodies: preparation and applications. Neuroprotocols, 1995, 6: 56-61.
Czernik, et al. Production of phosphorylation state-specific antibodies. Methods Enzymol. 1991;201:264-83.
Dzamko, et al. Inhibition of LRRK2 kinase activity leads to dephosphorylation of Ser(910)/Ser(935), disruption of 14-3-3 binding and altered cytoplasmic localization. Biochem J. Sep. 15, 2010;430(3):405-13.
European search report and opinion dated Oct. 7, 2014 for EP Application No. 12785566.6.
Forno, L.S. Neuropathology of Parkinson's disease. J Neuropathol Exp Neurol. Mar. 1996;55(3):259-72.
Gelb, et al. Diagnostic criteria for Parkinson disease. Arch Neurol. Jan. 1999;56(1):33-9.
Greggio, et al. Leucine-rich repeat kinase 2 and alpha-synuclein: intersecting pathways in the pathogenesis of Parkinson's disease? Mol Neurodegener. Jan. 18, 2011;6(1):6.
Hutton, et al. Association of missense and 5'-splice-site mutations in tau with the inherited dementia FTDP-17. Nature 393, 702-705 (Jun. 18, 1998) | doi:10.1038/31508; Received Apr. 9, 1998; Accepted Jun. 1, 1998.

(Continued)

*Primary Examiner* — John Ulm
(74) *Attorney, Agent, or Firm* — Wilson, Sonsini, Goodrich & Rosati

(57) ABSTRACT

Disclosed are novel phosphorylation sites identified in LRRK2 and associated with Parkinson's Disease, antibodies that specifically bind to the novel phosphorylation sites, and laboratory and clinical uses thereof.

17 Claims, 21 Drawing Sheets

(56) References Cited

OTHER PUBLICATIONS

International search report and written opinion dated Aug. 24, 2012 for PCT Application No. US2012/38696.

Jellinger. A critical evaluation of current staging of alpha-synuclein pathology in Lewy body disorders. Biochem. Et Biophys, Acta. 2009; 1792:730-740.

Kalaitzakis, et al. Controversies over the staging of alpha-synuclein pathology in Parkinson's disease. Acta Neuropathol. Jul. 2008;116(1):125-8; author reply 129-31. doi:10.1007/s00401-008-0381-3. Epub Apr. 30, 2008.

Kohler, et al. Continuous cultures of fused cells secreting antibody of predefined specificity. Nature. Aug. 7, 1975;256(5517):495-7.

Kozbor, et al. Specific immunoglobulin production and enhanced tumorigenicity following ascites growth of human hybridomas. J Immunol Methods. Jul. 16, 1985;81(1):31-42.

Lerner, RA. Tapping the immunological repertoire to produce antibodies of predetermined specificity. Nature. Oct. 14, 1982;299(5884):593-6.

Li, et al. Phosphorylation-dependent 14-3-3 binding to LRRK2 is impaired by common mutations of familial Parkinson's disease. PLoS One. Mar. 1, 2011;6(3):e17153.

Li, et al. Reevaluation of phosphorylation sites in the Parkinson disease-associated leucine-rich repeat kinase 2. J Biol Chem. Sep. 17, 2010;285(38):29569-76. Epub Jul. 1, 2010

Mage, et al. Preparation of Fan and F(ab')2 fragments from monoclonal antibodies. Monoclonal Antibody Production Techniques and Applications, 1987, Marcel Dekker, Inc.: New York, ch. 6 pp. 79-97.

Morrison, et al. Chimeric human antibody molecules: mouse antigen-binding domains with human constant region domains. Proc Natl Acad Sci U S A. Nov. 1984;81(21):6851-5.

Nairn, et al. Serum antibodies that distinguish between the phospho- and dephospho-forms of a phosphoprotein. Nature. Oct. 21, 1982;299(5885):734-6.

Neuberger, et al. Recombinant antibodies possessing novel effector functions. Nature. Dec. 13-19, 1984;312(5995):604-8.

Nguyen, et al. LRRK2 mutant iPSC-derived DA neurons demonstrate increased susceptibility to oxidative stress. Cell Stem Cell. Mar. 4, 2011;8(3):267-80. doi:10.1016/j.stem.2011.01.013.

Spillantini, et al. Alpha-synuclein in Lewy bodies. Nature. Aug. 28, 1997;388(6645):839-40.

Takeda, et al. Construction of chimaeric processed immunoglobulin genes containing mouse variable and human constant region sequences. Nature. Apr. 4-10, 1985;314(6010):452-4.

Toomik, et al. Protein kinase assay using tritiated peptide substrates and ferric adsorbent paper for phosphopeptide binding. Anal Biochem. Mar. 1993;209(2):348-53.

Walker, et al. Interaction of human IgG chimeric antibodies with the human FcRI and FcRII receptors: requirements for antibody-mediated host cell-target cell interaction. Mol Immunol. Apr. 1989;26(4):403-11.

White, et al. Preparation and use of anti-phosphotyrosine antibodies to study structure and function of insulin receptor. Methods in Enzymology, 1991, 201: 65-67.

Zhang, et al. Phosphoprotein analysis using antibodies broadly reactive against phosphorylated motifs. J Biol Chem. Oct. 18, 2002;277(42):39379-87. Epub Jul. 31, 2002

| | Antibody | Source | Epitope/immunogen |
|---|---|---|---|
| Total LRRK2 | Total LRRK2 | Sheep | 2498-2513 |
| | Total LRRK2 | Mouse | 2499-2514 |
| | Total LRRK2 | Sheep | 100-500 |
| | Total LRRK3 | Rabbit | 100-500 |
| | Total LRRK2 | Rabbit | near LRR |
| | Total LRRK2 | Rabbit | 1838-2133 |
| | Total LRRK2 | Rabbit | 1518-1638 |
| Phosphorlyated LRRK2 | pSer910 | Sheep | phospho Serine 910 |
| | pSer910 | Rabbit | phospho Serine 910 |
| | pSer935 | Sheep | phospho Serine 935 |
| | pSer935 | Rabbit | phospho Serine 935 |
| | pSer955 | Rabbit | phospho Serine 955 |
| | pSer973 | Rabbit | phospho Serine 973 |

Figure 8

| ▼A // B▶ | 1 | 2 | 3 | 4 | 5 | 6 | 7 | 8 | GST |
|---|---|---|---|---|---|---|---|---|---|
| 1 (mAb) | | 2 | 3 | 4 | 5 | 6 | 7 | 8 |
| 2 (mAb) | | | 9 | 10 | 11 | 12 | 13 | 14 | 15 |
| 3 | | | 37 | 16 | 17 | 18 | 19 | 20 | 21 |
| 4 | | | | 38 | 22 | 23 | 24 | 25 | 26 |
| 5 | | | | | 39 | 27 | 28 | 29 | 30 |
| 6 | | | | | | 40 | 31 | 32 | 33 |
| 7 | | | | | | | 41 | 34 | 35 |
| 8 | | | | | | | | 42 | 36 |
| GST | | | | | | | | | |

Figure 9

SEQ ID NO: 8 to 11 in order of appearance

SEQ ID NO: 12 to 15 in order of appearance

S910 FLVKKKSNSISVGEFYRD
S935 PNLQRHSNSLGPIFDHED
S955 KRKRKILSSDDSLRSSKL
S973 QSHMRHSDSISSLASERE

Figure 16

SEQUENCE LISTING

```
<160> NUMBER OF SEQ ID NOS: 15

<210> SEQ ID NO 1
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: Phosphoserine

<400> SEQUENCE: 1

Cys Leu Val Lys Lys Lys Ser Asn Ser Ile Ser Val Gly Glu
1               5                   10

<210> SEQ ID NO 2
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (8)..(8)
<223> OTHER INFORMATION: Phosphoserine

<400> SEQUENCE: 2

Cys Leu Gln Arg His Ser Asn Ser Leu Gly Pro Ile Phe Asp His
1               5                   10                  15

<210> SEQ ID NO 3
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: Phosphoserine

<400> SEQUENCE: 3

Cys Arg Lys Arg Lys Ile Leu Ser Ser Asp Asp Ser Leu Arg
1               5                   10

<210> SEQ ID NO 4
<211> LENGTH: 17
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (8)..(8)
<223> OTHER INFORMATION: Phosphoserine
<220> FEATURE:
<221> NAME/KEY: MOD_RES
<222> LOCATION: (11)..(11)
<223> OTHER INFORMATION: Phosphoserine

<400> SEQUENCE: 4

Cys His Met Arg His Ser Asp Ser Ile Ser Ser Leu Ala Ser Glu Arg
1               5                   10                  15

Glu

<210> SEQ ID NO 5
<211> LENGTH: 21
<212> TYPE: PRT
<213> ORGANISM: Unknown
<220> FEATURE:
<223> OTHER INFORMATION: Long variant LRRKtide peptide substrate

<400> SEQUENCE: 5

Arg Leu Gly Arg Asp Lys Tyr Lys Thr Leu Arg Gln Ile Arg Gln Gly
1               5                   10                  15

Asn Thr Lys Gln Arg
            20

<210> SEQ ID NO 6
<211> LENGTH: 21
<212> TYPE: PRT
<213> ORGANISM: Unknown
<220> FEATURE:
<223> OTHER INFORMATION: Nictide peptide substrate

<400> SEQUENCE: 6

Arg Leu Gly Trp Trp Arg Phe Tyr Thr Leu Arg Arg Ala Arg Gln Gly
1               5                   10                  15

Asn Thr Lys Gln Arg
            20

<210> SEQ ID NO 7
<211> LENGTH: 36
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<223> OTHER INFORMATION: N-term biotin
<220> FEATURE:
<221> NAME/KEY: MOD_RES
<222> LOCATION: (6)..(6)
<223> OTHER INFORMATION: Phosphoserine
<220> FEATURE:
<221> NAME/KEY: MOD_RES
<222> LOCATION: (31)..(31)
<223> OTHER INFORMATION: Phosphoserine

<400> SEQUENCE: 7

Lys Lys Lys Ser Asn Ser Ile Ser Val Gly Glu Phe Tyr Arg Asp Ala
1               5                   10                  15

Val Leu Gln Arg Cys Ser Pro Asn Leu Gln Arg His Ser Asn Ser Leu
            20                  25                  30

Gly Pro Ile Phe
```

<210> SEQ ID NO 8
<211> LENGTH: 67
<212> TYPE: DNA
<213> ORGANISM: Unknown
<220> FEATURE:
<223> OTHER INFORMATION: LRRK2 G2019S allele oligonucleotide

<400> SEQUENCE: 8
cttttcacac tgtatcccaa tgctgccatc attgcaaaga ttgctgacta cagcattgct    60
cagtact                                                              67

<210> SEQ ID NO 9
<211> LENGTH: 67
<212> TYPE: DNA
<213> ORGANISM: Unknown
<220> FEATURE:
<223> OTHER INFORMATION: LRRK2 G2019S allele oligonucleotide

<400> SEQUENCE: 9
agtactgagc aatgctgtag tcagcaatct ttgcaatgat ggcagcattg ggatacagtg    60
tgaaaag                                                              67

<210> SEQ ID NO 10
<211> LENGTH: 67
<212> TYPE: DNA
<213> ORGANISM: Unknown
<220> FEATURE:
<223> OTHER INFORMATION: LRRK2 G2019S allele oligonucleotide

<400> SEQUENCE: 10
cttttcacac tgtatcccaa tgctgccatc attgcaaaga ttgctgacta cggcattgct    60
cagtact                                                              67

<210> SEQ ID NO 11
<211> LENGTH: 67
<212> TYPE: DNA
<213> ORGANISM: Unknown
<220> FEATURE:
<223> OTHER INFORMATION: LRRK2 G2019S allele oligonucleotide

<400> SEQUENCE: 11
agtactgagc aatgccgtag tcagcaatct ttgcaatgat ggcagcattg ggatacagtg    60
tgaaaag                                                              67

<210> SEQ ID NO 12
<211> LENGTH: 18
<212> TYPE: PRT
<213> ORGANISM: Artificial Sequence
<220> FEATURE:
<223> OTHER INFORMATION: Synthetic peptide

<400> SEQUENCE: 12

Phe Leu Val Lys Lys Lys Ser Asn Ser Ile Ser Val Gly Glu Phe Tyr
1               5                   10                  15

Arg Asp

<210> SEQ ID NO 13
<211> LENGTH: 18
<212> TYPE: PRT
<213> ORGANISM: Artificial Sequence
<220> FEATURE:

```
<223> OTHER INFORMATION: Synthetic peptide

<400> SEQUENCE: 13

Pro Asn Leu Gln Arg His Ser Asn Ser Leu Gly Pro Ile Phe Asp His
1               5                   10                  15

Glu Asp

<210> SEQ ID NO 14
<211> LENGTH: 18
<212> TYPE: PRT
<213> ORGANISM: Artificial Sequence
<220> FEATURE:
<223> OTHER INFORMATION: Synthetic peptide

<400> SEQUENCE: 14

Lys Arg Lys Arg Lys Ile Leu Ser Ser Asp Asp Ser Leu Arg Ser Ser
1               5                   10                  15

Lys Leu

<210> SEQ ID NO 15
<211> LENGTH: 18
<212> TYPE: PRT
<213> ORGANISM: Artificial Sequence
<220> FEATURE:
<223> OTHER INFORMATION: Synthetic peptide

<400> SEQUENCE: 15

Gln Ser His Met Arg His Ser Asp Ser Ile Ser Ser Leu Ala Ser Glu
1               5                   10                  15

Arg Glu
```

ASSAY TO DETERMINE LRRK2 ACTIVITY IN PARKINSON'S DISEASE

This application claims priority from U.S. Provisional Application 61/487,628, filed May 18, 2011, U.S. Provisional Application 61/487,639, filed May 18, 2011, and U.S. Provisional Application 61/537,463, filed Sep. 21, 2011, the entire contents of each of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on May 7, 2015, is named 16817620881_ $sт$25.txt and is 4.98 kB in size.

BACKGROUND OF THE INVENTION

Parkinson's disease (PD) is a progressive neurodegenerative disease affecting 1-2% of the population over 65 years of age. It is estimated that the number of prevalent cases of PD world-wide will double by the year 2030. Currently, there is no cure, early detection mechanism, preventative treatment, or effective way to slow disease progression. The increasing disability caused by the progression of disease burdens the patients, their caregivers as well as society. Classic neuronal pathological features of PD include the loss of dopaminergic (DA) neurons in the substantia nigra (SN) and the presence of cytoplasmic inclusions known as Lewy bodies. Classical clinical features of PD include resting tremor, bradykinesia and rigidity, but the disease is now know to have wide variety of non-motor features such as autonomic dysfunction and dementia. Although the pattern of neuronal loss in PD is well characterized, the molecular mechanisms that lead to that cell death are still unknown. The majority of PD patients suffer from idiopathic disease with no clear etiology, and approximately 5% of patients present with familial PD.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 8 is a table listing antibodies against total LRRK2 protein or phosphorylated LRRK, and their sources.

FIG. 9 illustrates a sample matrix experiment for testing of total LRRK2 Assay Probes.

FIG. 16 shows primary amino acid sequence surrounding Serines 910, 935, 955 and 973.

DETAILED DESCRIPTION OF THE INVENTION

Parkinson's Disease (PD) is a movement disorder characterized by gradually progressing bradykinesia, resting tremor, and postural instability with an age-related onset [Gelb et al., Arch. Neurol. 56, 33-39 (1999)]. In its typical manifestation, it involves primarily the degeneration and loss of dopaminergic neurons in the substantia nigra, resulting eventually in severe deficiency of the neurotransmitter dopamine This type of neurodegeneration involves the formation of intracellular inclusion bodies (Lewy bodies) [Formo, J. Neuropathol. Exp. Neurol. 55, 259-272 (1996)], which contain the protein synuclein as a major constituent [Spillantini et al., Nature 388, 839-840 (1997); Baba et al., Am. J. Pathol. 152, 879-884 (1998)]. PD can therefore be classified as a distinct protein aggregation disorder affecting specific subpopulations of neurons.

Besides classical PD, Parkinsonism-related disorders have been defined with similar impairment of movement as in PD, but extended symptomatology involving also memory and cognitive functions. In such cases Lewy body formation has spread to cortical areas as well, providing for considerable diagnostic overlap with Dementia with Lewy bodies (DLB). Because of the pervasive involvement of synuclein in Lewy body formation, these diverse disorders are grouped under the term Synucleopathies. In spite of this conspicuous association, however, Lewy bodies may be more of a classification feature, reporting a specific pathobiochemistry, rather than a direct cause of neurodegeneration [Jellinger, Biochem. Biophys, Acta 2008; Parkinnen et al., Acta Neuropathol. 116, 125-128 (2008)]. On the other hand, the observed commonalities do suggest that certain forms of Parkinson's Disease with Dementia (PDD) are mechanistically related to classical PD. However, there are also forms of PDD with completely unrelated disease biology involving a different form of neurodegeneration based on the pathobiochemistry of the microtubule-associated protein tau (tauopathy), as most clearly exemplified by Frontotemporal Dementia with Parkinsonism caused by mutations in tau protein on chromosome 17 (FTDP-17) [Hutton et al., Nature 393, 702705 (1998)]. Hence, in view of the evolving molecular insights into the basis of these neurological disorders the classical clinical diagnoses will become more advantageously replaced by disease-mechanism based classifications, especially if the therapeutic consequences of diagnosis are increasingly less oriented on symptom relief but rather on causative treatment strategies. PD can present with an unknown etiology (idiopathic or sporadic PD) or from patients with a family history of PD (familial PD).

Figure 1:
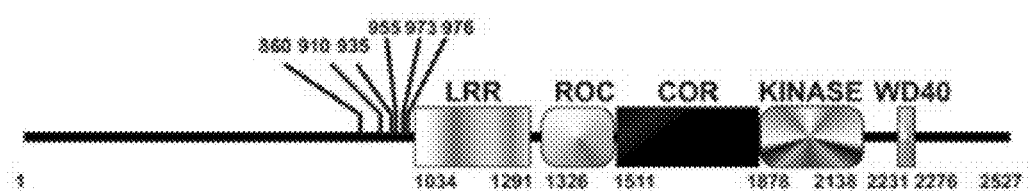
FIG. 1 illustrates domain structure of LRRK2 is to scale, with amino acid residues indicating domain boundaries and phosphorylation sites indicated.

Patients with mutations in the LRRK2 gene generally develop PD with clinical symptoms indistinguishable from idiopathic PD at around 60-70 years of age. Mutations in LRRK2 are the most common genetic cause of parkinsonism. As shown in FIG. 1, the LRRK2 gene encodes a large enzyme with an ankyrin repeat region, a leucine-rich repeat (LRR) domain, a serine/threonine kinase domain, a DFG-like motif, a RAS of complex proteins (ROC) domain, a GTPase domain, an MLK-like domain, a COR domain, and a WD40 domain.

More than 40 missense mutations have been reported that are located throughout the LRRK2 sequence and several mutants have been shown to segregate with disease [R1441C/G, Y1699C, G2019S and I2020T]. Of these, the most common mutation is the G2019S substitution, which increases kinase activity 2-3 fold, and R1441C/G/H, Y1699C and I2020T can induce the formation of cytoplasmic aggregates.

The cellular processes which are regulated by LRRK2, or the processes that regulate LRRK2 have yet to be elucidated. One hindrance to the efforts to understand the molecular mechanisms causing PD is the lack of biochemical understanding of the events that lead to the loss of substantia nigra neurons and other affected areas. Attribution of familial PD to mutations in specific genes presents the opportunity for dissecting of the cause of neuronal loss if we can gain an understanding of the perturbed function of the mutated gene products.

LRRK2 contains phosphorylation sites that can be described as either autophosphorylation sites or constitutive sites of modification. Autophosphorylation sites have the potential to serve as indicators of LRRK2 kinase activity, and are generally found in the ROC and COR domain of LRRK2. Constitutive phosphorylation sites hold the potential to provide reference points for identifying upstream and downstream signalling pathways for LRRK2 and are generally localized in a cluster preceding the LRR domain. Serines 860, 910, 935, 955 and 973/976 comprise the most commonly identified sites in this region and these are depicted in FIG. 1.

Substrate sequence analysis predicts that LRRK2 prefers to modify Thr residues in the context of a Nictide peptide substrate. Constitutive phosphorylation sites are all serines whereas autophosphorylation sites are predominantly threonine residues, supporting the idea that constitutive sites are not autophosphorylation sites.

LRRK2 interacts with a protein known as 14-3-3, which binds a multitude of functionally diverse signaling proteins, including kinases, phosphatases, and transmembrane receptors. The name 14-3-3 refers to the particular elution and migration pattern of these proteins on DEAE-cellulose chromatography and starch-gel electrophoresis. The 14-3-3 proteins eluted in the 14th fraction of bovine brain homogenate and are found on positions 3.3 of subsequent electrophoresis. Perturbed levels of 14-3-3 protein may be found in the cerebrospinal fluid of patients with neurodegenerative diseases.

LRRK2 interacts with 14-3-3 isoforms via phosphorylation of Ser910 and Ser935. The modification of serines 910 and 935 is likely carried out by an upstream kinase that is indirectly controlled by LRRK2. Treatment of cells with LRRK2 inhibitors induces dephosphorylation of Ser910 and Ser935 and causes LRRK2 to accumulate in cytoplasmic aggregates. Phosphorylation of Ser955 and Ser973 is dependent on LRRK2 kinase activity in a manner similar to that of Ser910 and Ser935. Additionally, phosphorylation of Ser955 and 973 is disrupted in the context of several PD associated mutations that induce LRRK2 aggregation and loss of 14-3-3 binding. Phosphorylation of Ser973 exhibits a non-reciprocal dependence on phosphorylation of Ser910/935. Therefore, Ser955 and Ser973 are two sites of LRRK2 modification that can be utilized as readouts of LRRK2 kinase activity.

While preferable embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention.

The invention provides methods for detecting phosphorylation of LRRK2 and applications thereof Various aspects of the invention described herein may be applied to any of the particular applications set forth below or for any other types of diagnostic or therapeutic applications. The invention may be applied as a standalone composition or method, or as part of an integrated pre-clinical, clinical, laboratory or medical application. It shall be understood that different aspects of the invention can be appreciated individually, collectively, or in combination with each other.

The compositions and methods herein can provide effective means for detection of phosphorylation of LRRK2 useful for a wide variety of applications including, for example, determination of LRRK2 phosphorylation status in vitro, in vivo, or in situ. Such determinations can be made in a broad array of biological samples such as those comprising or derived from a tissue or a populations of cells isolated from a subject. Cell lines derived from such samples may also be of particular use and can be maintained in undifferentiated state or differentiated to specific cell types such as neuronal cells or neurons. For example, the present compositions and methods can be used to detect LRRK2 phosphorylation in a population of induced pluripotent stem cells (iPSCs) derived from subjects bearing or not bearing a PD-associated mutation in LRRK2.

Another aspect of the invention provides methods of elucidating signaling pathways involving LRRK2 phosphorylation. Signaling pathways include proteins or other molecules that contribute to or are affected by LRRK2 phosphorylation. Such molecules generally include kinases and phosphatases as well as proteins that interact with LRRK2 in a phosphorylation-dependent or phosphorylation-independent manner. Embodiments of the invention provide for methods of determining relationships between such molecules to elucidate signaling pathways involving LRRK2 phosphorylation.

Methods of the invention can also be applied to determine functional roles of LRRK2 phosphorylation. For example, the kinase activity of LRRK2 can be studied with respect to its phosphorylation as determined using the compositions and methods herein. Embodiments of the invention are also suitable for studying other functional parameters, such as, for example, the effect of LRRK2 phosphorylation on autophagy, apoptosis, expression levels of LRRK2 or other proteins, localization of LRRK2 or other proteins, or aggregation of LRRK2 or other proteins.

In some aspects, disclosed compositions and methods are used in conjunction with use of LRRK2 inhibitors and substrates. Methods for identifying and using inhibitors and substrates of LRRK2 are described in U.S. Patent Publication Ser. No. 2010/0068742 and PCT Publication Ser. No. WO/2010/031988, each of which is incorporated herein by reference in its entirety for all purposes. Some LRRK2 inhibitors are known, and have been described in US 2010/0273769 A1 and US 2009/0004112 A1.

The compositions and methods herein have a broad spectrum of utility in clinical applications including, for example, diagnosis of PD, prognosis of PD, determination of treatment efficacy for PD, and selection of a treatment regimen for a subject suffering from PD.

Phospho-Specific Antibodies

In one aspect, the disclosure provides an isolated phospho-specific antibody that specifically binds LRRK2 only when phosphorylated at a regulatory site. This subset of embodiments includes, but is not limited to, antibodies specific for phospho-LRRK2 (Ser910), phospho-LRRK2 (Ser935), phospho-LRRK2 (Ser955), and phospho-LRRK2 (Ser973). Phospho-specific antibodies that recognize a single phosphorylation site can be used individually, or they can be used in combination with other antibodies or phospho-specific antibodies.

The term phospho-specific antibody refers to an antibody that specifically recognizes and binds to one or more phosphorylated residues of a phosphorylated substrate molecule. The phosphorylated residue that is recognized by the specific antibody can be a phosphorylated tyrosine, a phosphorylated serine, a phosphorylated threonine or a phosphorylated histidine.

Suitable antibodies may be any intact immunoglobulin molecules or fragments thereof (i.e., active portions of immunoglobulin molecules) that are capable of specifically recognizing and binding to an epitope of a phosphorylated substrate molecule. The type of antibody that can be used in the inventive methods may be either monoclonal (recognizing one epitope of its target) or polyclonal (recognizing multiple epitopes).

Phospho-specific antibodies for use in the practice of the assay and screening methods of the invention may be produced or purchased from different commercial resources. As will be appreciated by one of ordinary skill in the art, any type of antibody can be generated and/or modified to specifically recognize and bind to an epitope of a substrate molecule phosphorylated at one or more tyrosine, serine, threonine or histidine residues.

Methods for producing custom polyclonal antibodies are well known in the art and include standard procedures such as immunization of rabbits or mice with pure protein or peptide (see, for example, R. G. Mage and E. Lamoyi, in "Monoclonal Antibody Production Techniques and Applications", 1987, Marcel Dekker, Inc.: New York, pp. 79-97). Anti-phosphoserine polyclonal antibodies can, for example, be made using the techniques described by M. F. White and J. M. Backer (as described in Methods in Enzymology, 1991, 201: 65-67, which is incorporated herein by reference in its entirety).

Monoclonal antibodies that specifically bind to a phosphorylated substrate may be prepared using any technique that provides for the production of antibody molecules by continuous cell lines in culture. These techniques include, but are not limited to, the hydroma technique, the human B-cell hydroma technique, and the EBV-hydroma technique (see, for example, G. Kohler and C. Milstein, Nature, 1975, 256: 495-497; D. Kozbor et al, J. Immunol. Methods, 1985, 81: 31-42; and R. J. Cote et al, Proc. Natl. Acad. Sci. 1983, 80: 2026-2030). Monoclonal antibodies may also be made by recombinant DNA methods (see, for example, U.S. Pat. No. 4,816,567). Other methods have been reported and can be employed to produce monoclonal antibodies for use in the practice of the invention (see, for example, R. A. Lerner, Nature, 1982, 299: 593-596; A. C. Nairn et al. Nature, 1982, 299: 734-736; A. J. Czemik et al. Methods Enzymol. 1991, 201: 264-283; A. J. Czernik et al, Neuromethods: Regulatory Protein Modification: Techniques & Protocols, 1997, 30: 219-250; A. J. Czernik et al, Neuroprotocols, 1995, 6: 56-61; and H. Zhang et al, J. Biol. Chem. 2002, 277: 39379-39387).

Techniques developed for the production of chimeric antibodies, the slicing of mouse antibody genes to human antibody genes to obtain a molecule with appropriate specificity and biological activity, can, alternatively, be used in the preparation of antibodies (S. L. Morrison et al, Proc. Natl. Acad. Sci, 1984, 81: 6851-6855; M. S. Neuberger et al. Nature, 1984, 312: 604-608; S. Takeda et al. Nature, 1985, 314: 452-454). Monoclonal and other antibodies can also be "humanized"; sequence differences between rodent antibodies and human sequences can be minimized by replacing residues which differ from those in the human sequences by site-directed mutagenesis of individual residues or by grafting of entire complementarity determining regions. Humanized antibodies can also be produced using recombinant methods (see, for example, GB 2 188 638 B).

Antibodies to be used in the methods of the invention can be purified by methods well known in the art (see, for example, S. A. Minden, "Monoclonal Antibody Purification", 1996, IBC Biomedical Library Series: Southbridge, Mass.). For example, antibodies can be affinity-purified by passage over a column to which a phosphorylated substrate molecule is bound. The bound antibodies can then be eluted from the column using a buffer with a high salt concentration.

Included in the scope of the invention are equivalent non-antibody molecules, such as protein binding domains or nucleic acid aptamers, which bind, in a phospho-specific manner, to essentially the same phosphorylatable epitope to which the phospho-specific antibodies of the invention bind. See, e.g., Neuberger et al., Nature 312: 604 (1984). Such equivalent non-antibody reagents may be suitably employed in the methods of the invention further described below. Antibodies provided by the invention may be any type of immunoglobulins, including IgG, IgM, IgA, IgD, and IgE, including Fab or antigen-recognition fragments thereof The antibodies may be monoclonal or polyclonal and may be of any species of origin, including (for example) mouse, rat, rabbit, horse, or human, or may be chimeric antibodies. See, e.g., M. Walker et al., Molec. Immunol. 26: 403-11 (1989); Morrision et al., Proc. Nat'l. Acad. Sci. 81: 6851 (1984); Neuberger et al., Nature 312: 604 (1984)). The antibodies may be recombinant monoclonal antibodies produced according to the methods disclosed in U.S. Pat. No. 4,474,893 or U.S. Pat. No. 4,816,567. The antibodies may also be chemically constructed by specific antibodies made according to the method disclosed in U.S. Pat. No. 4,676,980.

The invention also provides immortalized cell lines that produce an antibody of the invention. For example, hybridoma clones, constructed as described above, that produce monoclonal antibodies to the protein phosphorylation sites disclosed herein are also provided. Similarly, the invention includes recombinant cells producing an antibody of the invention, which cells may be constructed by well known techniques; for example the antigen combining site of the monoclonal antibody can be cloned by PCR and single-chain antibodies produced as phage-displayed recombinant antibodies or soluble antibodies in *E. coli* (see, e.g., Antibody Engineering Protocols, 1995, Humana Press, Sudhir Paul editor.)

Phosphorylation site-specific antibodies of the invention, whether polyclonal or monoclonal, may be screened for epitope and phospho-specificity according to standard techniques. See, e.g. Czernik et al., Methods in Enzymology, 201: 264-283 (1991). For example, the antibodies may be screened against the phospho and non-phospho peptide library by ELISA to ensure specificity for both the desired antigen and for reactivity only with the phosphorylated (or non-phosphorylated) form of the antigen. Peptide competition assays may be carried out to confirm lack of reactivity with other phosphoepitopes on the given Target Signal Protein/Polypepetide.

The antibodies may also be tested by Western blotting against cell preparations containing the signaling protein, e.g. cell lines over-expressing the target protein, to confirm reactivity with the desired phosphorylated epitope/target.

In an exemplary embodiment, phage display libraries are used for high-throughput production of monoclonal antibodies that target post-translational modification sites (e.g., phosphorylation sites) and, for validation and quality control, high-throughput immunohistochemistry is utilized to screen the efficacy of these antibodies. Western blots, protein microarrays and flow cytometry can also be used in high-throughput screening of phosphorylation site-specific polyclonal or monoclonal antibodies of the present invention. See, e.g., Blow N., Nature, 447: 741-743 (2007).

Specificity against the desired phosphorylated epitope may also be examined by constructing mutants lacking phosphorylatable residues at positions outside the desired epitope that are known to be phosphorylated, or by mutating the desired phospho-epitope and confirming lack of reactivity. Phosphorylation-site specific antibodies of the invention may exhibit some limited cross-reactivity to related epitopes in non-target proteins. This is not unexpected as most antibodies exhibit some degree of cross-reactivity, and anti-peptide antibodies will often cross-react with epitopes having high homology to the immunizing peptide. Cross-reactivity with non-target proteins is readily characterized by Western blotting alongside markers of known molecular weight Amino acid sequences of cross-reacting proteins may be examined to identify sites highly homologous to the target signaling protein/polypeptide epitope for which the antibody of the invention is specific.

In certain cases, polyclonal antisera may exhibit some undesirable general cross-reactivity to phosphotyrosine or phosphoserine itself, which may be removed by further purification of antisera, e.g., over a phospho tyramine column Antibodies of the invention specifically bind their target protein only when phosphorylated (or only when not phosphorylated, as the case may be) and do not (substantially) bind to the other form (as compared to the form for which the antibody is specific).

In some embodiments, total LRRK2 antibodies are used for comparison to phospho-specific LRRK2 antibodies. Total LRRK2 antibodies have been produced in various organisms including mouse (available for purchase from Sigma) and rabbit (available for purchase from Sigma and Enzo Life Sciences), as well as sheep. Phospho-specific LRRK2 antibodies may be referred to herein by the designation "pSer [X]" where [X] represents a phosphorylated residue recognized by an antibody (e.g., pSer910, pSer935, pSer955, and pSer973).

Use of Phospho-Specific Antibodies

Methods of using antibodies for in vitro, in vivo, ex vivo, and in situ analysis are known. Conventional immunoassays include, without limitation, an ELISA, an RIA, FACS, tissue immunohistochemistry, Western blot or immunoprecipitation assays described in Harlow and Lane Antibodies: A Laboratory Manual, Cold Spring Harbor Laboratory Press, Cold Spring Harbor, N.Y. (1990).

Antibodies of the invention can be used to detect phospho-LRRK2 from humans. In another embodiment, the antibodies can be used to detect phospho-LRRK2 from primates such as cynomologus monkey, rhesus monkeys, chimpanzees or apes. The invention provides a method for detecting phospho-LRRK2 in a biological sample comprising contacting a biological sample with a phospho-specific antibody of the invention and detecting the bound antibody. In one embodiment, the phospho-specific antibody is directly labeled with a detectable label. In another embodiment, the phospho-specific antibody (the first antibody) is unlabeled and a second antibody or other molecule that can bind the phospho-specific antibody is labeled. As is well known to one of skill in the art, a second antibody is chosen that is able to specifically bind the particular species and class of the first antibody. For example, if the phospho-specific antibody is a human IgG, then the secondary antibody could be an antihuman-IgG. Other molecules that can bind to antibodies include, without limitation, Protein A and Protein G, both of which are available commercially, e.g., from Pierce Chemical Co.

Suitable labels for the antibody or secondary antibody include, but are not limited to, various enzymes, prosthetic groups, fluorescent materials, luminescent materials and radioactive materials. Examples of suitable enzymes include horseradish peroxidase, alkaline phosphatase, (3-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}I$, $^{131}I$, $^{35}S$ or $^{3}H$.

One can use the immunoassays disclosed above for a number of purposes. For example, the phospho-specific antibodies can be used to detect phospho-LRRK2 in cells or on the surface of cells in cell culture, or secreted into the tissue culture medium. The phospho-specific antibodies can be used to determine the amount of phospho-LRRK2 on the surface of cells or secreted into the tissue culture medium that have been treated with various compounds. This method can be used to identify compounds that are useful to inhibit or activate phospho-LRRK2 expression or localization. According to this method, one sample of cells is treated with a test compound for a period of time while another sample is left untreated. If the total level of phospho-LRRK2 is to be measured, the cells are lysed and the total phospho-LRRK2 level is measured using one of the immunoassays described above. The total level of phospho-LRRK2 in the treated versus the untreated cells is compared to determine the effect of the test compound.

In some embodiments, methods for in situ analysis of LRRK2 phosphorylation are provided.

Antibodies may be further characterized in this way using normal and diseased tissues to evaluate phosphorylation and activation status in diseased tissue. Also known as immunohistochemical analysis or immunohistochemistry (IHC), in situ analysis refers to the process of detecting antigens (e.g., proteins) in cells of a tissue section by exploiting the principle of antibodies binding specifically to antigens in biological tissues. IHC protocols are well known in the art; see, e.g., Immunocytochemical Methods and Protocols (second edition), edited by Lorette C. Javois, from Methods in Molecular Medicine, volume 115, Humana Press, 1999 (ISBN 0-89603-570-0) and U.S. Pat. Nos. 5,846,739 and 5,989,838. Briefly, paraffin-embedded tissue (e.g., tumor tissue) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary antibody and secondary antibody; and finally detecting using ABC avidin/biotin method according to manufacturer's instructions.

Antibodies may be further characterized by flow cytometry carried out according to standard methods. See Chow et al., Cytometry (Communications in Clinical Cytometry) 46: 72-78 (2001).

Proximity Ligation Assay

Compositions and methods of the invention can be applied to conduct a proximity ligation assay (PLA). PLA allows for increasing signal intensity for antibody recognition events by combining the specificity of antibody recognition with the signal amplification and detection of nucleic acids. Methods using PLA provide advantages in selectivity and sensitivity, aspects that are becoming increasingly necessary when probing sample sets that are derived from limited source material.

Figure 2:
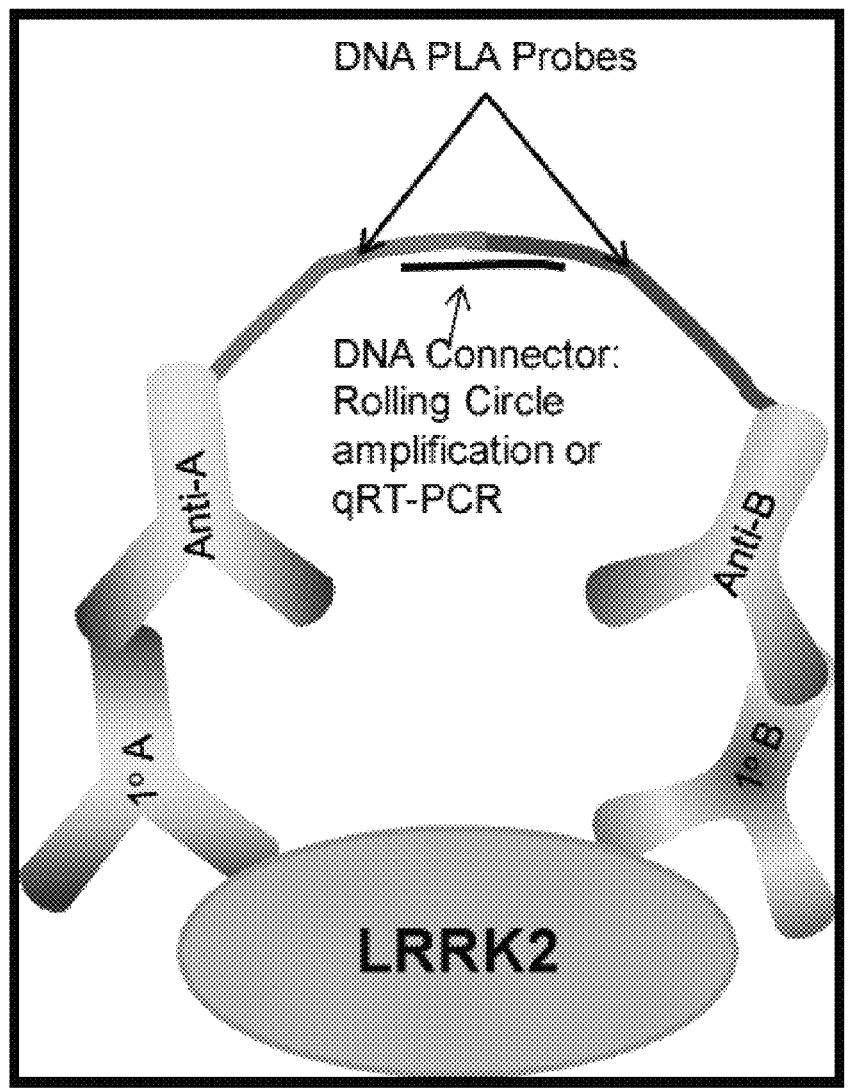
FIG. 2 depicts proximity ligation assay (PLA) detection of an antigen (e.g., LRRK2).

A schematic diagram of PLA is shown in FIG. 2. PLA enhances protein detection by antibodies. It does this by translating the interaction into detectable DNA molecules by employing secondary antibody:DNA conjugates. Species specific secondary antibodies conjugated to unique short DNA strands (PLA probes) are used to detect primary antibody detection of target protein. When two primary antibodies of different species are used (i.e. sheep anti-LRRK2 and rabbit anti-LRRK2 pSer910), the species specific PLA probes detect the primary antibodies, bringing the DNA strands of the PLA probes in close proximity. The proximity of the probes can be detected by either a subsequent addition of circle forming DNA oligonucleotides. Following ligation, the circle DNA is amplified by rolling circle amplification and is typically used in in situ studies. This localized concentration of fluorescent signal easily detectible in a fluorescent microscope. Ligations of connecting oligonucleotides are and then and detected using real time PCR. Additionally, this technique can be employed in solution where the PLAs are ligated using a connector oligonucleotide. These ligated PLA probes are then detected using quantitative real time PCR to amplify the connector region of the annealed probes in close spatial proximity.

PLA can be employed using methods or compositions of the invention in vitro, in vivo, ex vivo, or in situ. In some embodiments, PLA is performed using phospho-specific antibodies of the invention in situ.

Cell Types

Cells for analysis using compositions and methods of the invention can be derived from nervous tissue including, but not limited to brain stem, cerebrum, cerebellum, corpus callosum, glia, and spinal cord. In some embodiments, cells for analysis are derived from any tissue selected from the group consisting of lung, breast, stomach, pancreas, prostate, bladder, bone, ovary, skin, kidney, sinus, colon, intestine, stomach, rectum, esophagus, blood, brain and its coverings, spinal cord and its coverings, muscle, connective tissue, adrenal, parathyroid, thyroid, uterus, testis, pituitary, reproductive organs, liver, gall bladder, eye, ear, nose, throat, tonsils, mouth, and lymph nodes and lymphoid system.

Cell lines for use with the invention can be derived from a mammalian cell of origin. Suitable mammalian cells of origin include, but are not limited to, hamster, cattle, primate (including humans and monkeys) and dog cells. Various cell types may be used, such as kidney cells, fibroblasts, retinal cells, lung cells, etc. Among suitable cell lines the Human Embryonic Kidney cell line (HEK 293) is a common, transfectable cell line capable of high-level gene expression. HEK 293 cells may be especially useful for immunoassays with antibodies of the invention. The 3T3 standard fibroblast cell line can also be suitable. Many cell lines are widely available e.g. from the American Type Cell Culture (ATCC) collection, from the Coriell Cell Repositories, or from the European Collection of Cell Cultures (ECACC).

Cells can be derived from a subject and reprogrammed into induced pluripotent stem cells (iPSCs). These cells can then be differentiated into various cell types, including neuronal stem cells (NSCs) and dopaminergic (DA) neurons, representing a subject-derived neuronal model of PD. For example, fibroblasts from patients harboring heterozygous and homozygous LRRK2 mutation encoding the Glycine 2019 Serine mutation, as well as age matched controls can be employed. The differentiation of these cells to DA neurons represents an experimentally tractable model of PD in a culture dish. Methods of producing iPSCs are known and described in U.S. Patent Publication Ser. Nos. 2010/0041054, 2010/0167286, 2009/0324559, and 2010/0003757, herein incorporated by reference in their entireties.

ZFN-Mediated Genome Editing

ZFN-mediated genome editing can be used in conjunction with compositions and methods of the disclosure. ZFN-mediated methods of genome editing are known and described in U.S. Patent Publication Ser Nos. 2010/0055793, 2011/0086015, 2007/0218528, 2010/0257638, 2007/0218528, and 2009/0117617.

Figure 3:
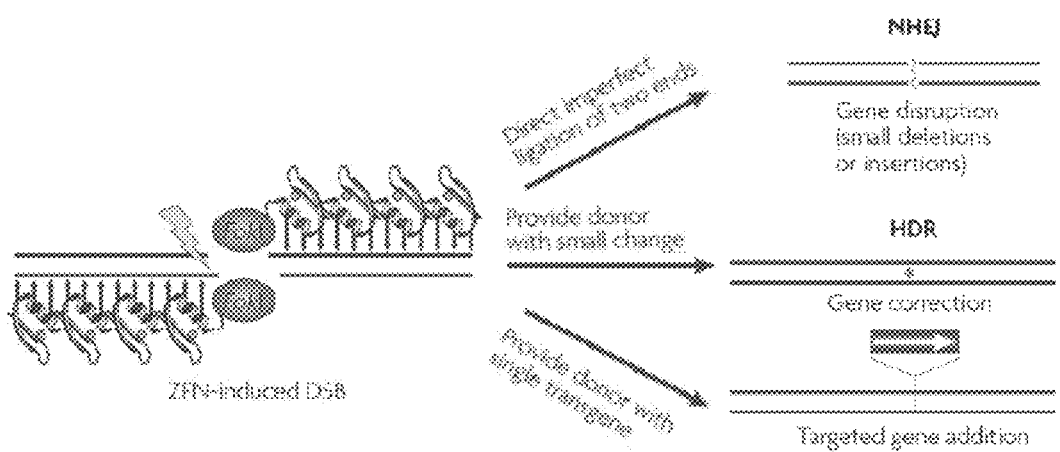
FIG. 3 depicts ZFN-driven genome editing.

ZFNs can be engineered to introduce targeted DNA double-strand break (DSB) at a locus of interest. ZFNs consist of a zinc finger DNA binding domain and the cleavage domain of the FokI restriction enzyme. The DNA binding domain, which contains a tandem array of 3-6 Cys2-His2 zinc fingers, is designed to target a 9-18 by site specified by the investigator (each finger recognizes ~3 by of DNA). Cleavage of DNA requires dimerization of the FokI domain, which is facilitated by designing two ZFNs that bind to adjacent sites (with typically a 5 or 6-bp gap between the 2 sites) with the correct orientation (FIG. 3). The resultant DSB is resolved through either the homology-directed repair (HDR) or non-homologous end joining (NHEJ) pathway, which can be exploited to perform precise base alteration (gene correction) or generate small deletions or insertions (gene disruption), respectively.

In some embodiments, ZFN-driven genome editing is used to correct the LRRK2 G2019S mutation in iPS cells. In some embodiments, ZFN-driven genome editing is used to create the LRRK2 G2019S mutation in iPS cells. ZFN-driven genome editing can be applied to produce any point mutation, insertion mutation, or deletion mutation within the LRRK2 gene. Further exemplary mutations that can be created or corrected using the technology include, but are not limited to, R1441C/G, Y1699C, I2020T, S910A, S910E/D, S935A, S935E/D, S955A, S955E/D, S973A, and S973E/D.

Alternatively, following cleavage by ZFNs, NHEJ-based repair can lead to efficient re-ligation of the broken ends without the requirement for a homologous donor; the gain or loss of genetic information that is typically associated with this process frequently leads to frameshift mutations (gene disruption). For example, the LRRK2 G2019S allele can be disrupted using the same method.

Kinase Assays

In some embodiments, a kinase assay is used to measure LRRK2 activity. Alternatively, a kinase assay may be used to measure phosphorylation of LRRK2. A kinase assay measures how much phosphorylation has been catalyzed by the kinase in a known amount of time. A simple presently known method of doing this is to provide one reactant of the phosphorylation reaction that provides a label which can be measured in the product (and the labelled product differentiated from the labelled reactant). This is commonly is done by providing radioactively labelled ATP, the use of which in the kinase reaction will result in radioactively labelled target peptide. Since the phosphoryl group transferred from ATP to the target peptide contains atoms of oxygen and phosphorous, it is theoretically possible to use radioactive isotopes of any of these atoms as the label. In practice, phosphorous (32P or 33P) is the preferred choice. In addition to direct radioactive labeling, there are indirect labeling or capture methods that exploit antibodies specific for the phosphorylated form of the peptide. This approach forms the basis of both radio-immunoassays and non-radiometric immunoassays. In the latter, the phosphopeptidespecific antibody (or secondary antibody) may carry an integral enzyme activity, such as horseradish peroxidase, which will allow detection by use of a chromogenic substrate, or, the antibody may carry some easily detected fluorophore or phosphor. If the substrate peptide includes an appropriate fluorophore that does not interfere with its suitability as a substrate, the phosphopeptide specific anti body can be employed in a fluorescence polarization detection scenario. Since the non-phosphorylated peptide will have more rapid rotational diffusion compared to phosphorylated peptide/antibody complex, these two forms of the substrate (unbound and antibody-bound) are distinguishable upon analysis using polarized light.

As is understood by those skilled in the art, in addition to the kinase enzyme itself and the necessary reactants, for effective and repeatable assay measurements it is also necessary that the reaction occur in an appropriate media composed of appropriate solvent(s), salts, and various factors that facilitate the reaction. Water is the preferred media, but other solvents may be used in whole or more preferably in combination with water. These include DMSO, ethanol, and other solvents known to those of skill in the art as being potentially compatible with enzymatic activity. Of course, it is preferred that buffers be included in the assay to maintain an appropriate pH range. Useful buffers include HEPES, Tris, MOPS, and the like. The pH is preferably about 6.3-8.3, and more preferably about 6.8-8.8. In a most preferred embodiment, the pH is about 7.3. It is important to include certain salts in the reaction mixture for optimal activity. In particular, it is preferred to include MgCl2 and MnCl2 at appropriate concentrations. Finally, certain surfactants, cofactors, and the like are preferably included. Among these are BSA or other stability-enhancing proteins, as well as EDTA or other heavy metal scavenging compounds.

Different substrates may be used, peptides or whole proteins, which may be natural or artificial substrates, including the LRRKtide and Nictide peptides. Also, the autophosphorylation of LRRK2 itself can be used as a measure of activity. Assays can be conducted at different concentrations of ATP, which may reflect physiological levels, or may prove advantageous with a particular assay technology. Other assay components may include co-substrates or regulatory molecules, including but not limited to GTP or non-hydrolysable analogs thereof LRRK2 assays may contain full-length protein, or an active fragment thereof, or various fusion protein constructs, e.g. containing tags commonly used for the convenience of purification, or may make use of mutants of LRRK2, preferably those which cause PD.

It is preferable to incubate the kinase reaction of the present assay at a temperature between 10-40° C. More preferably, the reaction occurs at between 25-40° C. Because it is preferred and easily achieved, the reaction is best incubated at about 30° C. This incubation period can last anywhere from a few minutes to a few hours, with a time period of 20 minutes to 90 minutes being preferred. In some embodiments, the incubation time is about 40 min, 50 min, 60 min, 70 min, 75 min, 80 min, 90 min, 100 min, 110 min or about 120 min.

After running the kinase assay, it is necessary to stop the enzyme reaction at a pre-determined time. If the reaction isn't stopped at a precise known time, then it isn't feasible to compare results from one reaction to another. Of course, any reasonable method of stopping the reaction may be utilized, as long as it doesn't interfere with accurate measurement of the kinase reaction results. For example, certain compounds may be added to the reaction mixture that rapidly denature, degrade, or otherwise disable the kinase enzyme. Such compounds include TCA, phosphoric acid, SDS, and the like. Alternatively, it may be feasible to heat the reaction mixture to the point where the kinase enzyme protein is permanently denatured. Such action would require heating to a temperature of at least about 65° C. Other suitable means are known to those skilled in the art.

After the kinase reaction is complete, and the kinase enzyme is disabled, isolation of the labelled target substrate is typically required. If the target substrate is not isolated, it is typically impossible to distinguish the signal generated by the labelled substrate from the signal generated by unused labelled reactant. In some cases, however, it is not necessary to isolate the labelled target substrate, and in such cases immediate measurement is performed. For example, in certain cases an assay such as a scintillation proximity assay may be performed, in which case isolation of the labelled substrate is unnecessary.

Those of skill in the art are aware of many means for isolating the labelled target substrate from the unused labelled reactant. Typical examples include gel electrophoresis, precipitation, filtration, chromatography, immunoprecipitation, and the like. Separation of the labelled target substrate can also be achieved by TCA precipitation of the target peptide.

An excellent method of separation is specific binding of the labelled target substrate to a solid support followed by washing away of the unused labelled reactant. For this method, a wide variety of solid substrates may be used Factors to be considered in selecting an appropriate substrate include the adhesion and functional retention of the immobilizing receptor, accessible surface area for binding, wash convenience, cost, high-throughput adaptability, etc. Frequently, the solid substrate will be the wall of the reaction reservoir itself. Preferred substrates maximize signal strength and the signal-to-noise ratio. Exemplary substrates include polystyrene microtiter plates, fine fibers, polymeric or silica-based microbeads, etc., preferably pre-activated to provide maximal protein binding. When used, microbeads are selected by size, range and structure to maximize surface area, filter retention and bead suspension time during the assay incubations.

Once the labelled target substrate is separated from unused labelled reactant, it is necessary to measure the amount of labelled target substrate. The means of making this measurement depend upon the type of label used. For radioactively labelled target substrates, the amount of radioactivity present is measured in any of a variety of means known to those of skill in the art, including scintillation counting, quantitative autoradiography, densitometry, phosphoimaging, and the like.

If the target substrate is labelled with a fluorescent label, then the amount of label may be measured by quantitative spectrophotometry, fluorescence/chemiluminescence imaging, or the like.

Other methods for detecting kinase activity are based on separations due to the charge differences between phosphorylated and non-phosphorylated proteins and peptides. In these respects, techniques based on gel electrophoresis and HPLC have, among others, been used. In combination with these techniques, spectrophotometric and fluorometric detection have been used. Reference is made to International Patent Application WO 93/10461 and U.S. Pat. Nos. 5,120,644 and 5,141,852 for descriptions of many methods heretofore used for detecting protein kinase activity. Also reference is made to Toomik et al., Analytical Biochemistry, 209:348-53 (1993).

While not strictly necessary, as a practical matter it is highly useful to include a series of controls for a kinase reaction. If a test compound is being added to one reaction mixture, it is important to add an identical volume of a similar composition (absent the test compound only) to a control kinase reaction. This will then account for any alterations in kinase activity caused by solvents, salts, or other components of the solution containing the test compound.

It is also very helpful to include positive and negative control kinase reactions that are likewise as similar as possible to the experimental reactions, but which contain known modulators of the kinase activity. By testing known inhibitors and agonists of the kinase activity alongside the unknown test compounds, it is easier to control for unforeseeable fluctuations in kinase responsiveness.

One important aspect of the present invention is its suitability for use in screening for modulators of LRRK2. Because the reaction is simple, performable in small volumes (e.g., on microtiter plates), and reproducible, it is possible to screen huge libraries of compounds and discover those that modulate LRRK2 phosphorylation in various manners. Such newly discovered modulators are potential pharmaceuticals for humans and animals.

Autophagy

Autophagy is a degradative mechanism involved in the recycling and turnover of cytoplasmic constituents from eukaryotic cells. This phenomenon of autophagy has been observed in neurons from patients with PD, suggesting a functional role for autophagy in neuronal cell death. Autophagic cell death involves accumulation of autophagic vacuoles (AVs) in the cytoplasm of dying cells as well as mitochondria dilation and enlargement of the endoplasmic reticulum and the Golgi apparatus. Autophagic cell death has been described during the normal nervous system development and could be a consequence of a pathological process such as those associated with neurodegenerative diseases. The formation of AV can be measured by the accumulation of the autophagosome marker LC3 to AV in discreet foci.

When autophagy is induced, the microtubule-associated protein 1 light chain 3 (LC3) is processed post-translationally into LC3-I, and then to LC3-II, which associates with autophagosome membranes. Quantification of the number of cells with LC3-positive vesicles or LC3-II levels (versus actin) allows for a specific and sensitive assessment of autophagosome number in large numbers of cells. Furthermore, as EGFP-LC3 overexpression does not affect autophagic activity, the numbers of EGFP-LC3 vesicles have frequently been used to assess autophagosome number. Overexpression of LRRK2 in HEK293 cells and in SH-SY5Y cells increases the number of multi-vesicular bodies and autophagic compartments Autophagy is another functional pathway that can be studied with respect to altered LRRK2 activity. Wild-type and mutant LRRK2 genotype can be studied for induction of autophagy or autophagic flux using multiple known methodologies. Induction of autophagy is accompanied by the accumulation of LC3 puncta in the cytoplasm of cells and can be easily visualized by immunofluorescence microscopy with commercially available antibodies. Comparing control lines versus LRRK2 mutant lines, it is possible to evaluate the number of endogenous LC3 puncta per cell using computer software such as NIH ImageJ or WatershedCounting3D. If mutant LRRK2 induces autophagy, these puncta should be more prevalent in the mutant lines and be potentially abrogated by LRRK2-IN1 treatment. Inducers of autophagy (nutrient starvation, mTORC1 inhibitors) can also be tested in these models to serve as positive controls for the assay, as well as evaluate whether altered LRRK2 kinase activity can negatively affect the onset of autophagy. A second measure of autophagy that is crucial to appropriate evaluation of LC3 puncta data is autophagic flux, which reveals the convergence of autophagic compartments with functional degradative compartments. Otherwise, LC3 accumulation could misinterpreted as an increase in the onset of autophagy instead of a disruption downstream of autophagy induction. A quenching assay can be used to detect the convergence of autophagic compartments with the late lysosomal compartments.

Here, de-quenched BSA is heavily labeled with BODIPY TR-X dye, resulting in self quenching of the fluorophore. This is incubated in the culture medium and will accumulate in lysosomes, where upon degradation, the fluorophore becomes fluorescent and indicative of functional lysosomes. Co-localization with LC3 is indicative of functional fusion of autophagic compartments with degradative compartments. The accumulation of p62, which should not occur if autophagy is active, can also be measured. Another parameter used to study autophagy is LC3 localization. A tandem green and red fluorescent protein-conjugated to LC3 can be used to detect LC3 localization. GFP-RFP-LC3 proteins localize to the autophagosome, which fuses with the lysosome to form the autolysosome, where degradation of cellular components occurs. Appropriate progression of autophagy brings the GFP-RFP-LC3 protein to the autolysosome where the GFP signal is quenched by the low pH. Therefore colocalization of RFP and GFP indicates no autophagy, and red fluorescence after autophagy induction indicates faithful maturation of the autophagosome. NSCs can be generated that stably express this fusion protein using lentiviral methods or standard electroporation and stable cell cloning. Following differentiation, these models can be subjected to the above analyses to assess the full impact of mutant LRRK2 on neuronal survival and autophagy as well as the efficacy of LRRK2-IN1 treatment.

Apoptosis

The term apoptosis is intended to mean the cascade of energy (ATP) dependent events triggered by an apoptosis inducer agent and leading to programmed cell death through mechanisms commonly involving intracellular caspase enzymes; commonly requiring about 12 to about 24 hrs.; and commonly involving cell death. In certain embodiments the invention provides methods for assessing apoptosis prior to cell swelling, fragmentation and/or lysis. Mechanistically, during apoptosis dying cells fragment their DNA and become fragmented themselves into membrane-bounded apoptotic bodies. The released apoptotic bodies are ultimately subject to phagocytosis by immune cells. Where potentially toxic products resulting from apoptotic cell death are removed by phagocytes, death of a cell commonly does not result in death of adjacent cells. Apoptosis is most definitively proven to have taken place by rescuing dying cells and bringing them back to a condition of growth by addition of an apoptosis inhibiting agent. Apoptosis is recognized to play a fundamental role in cell development, tissue renewal; generating and regulating immune responses; and, preventing malignant transformation. Apoptosis has been implicated in the pathogenesis of an increasing number of diseases and may contribute to neuronal loss resulting from acute insults, such as ischemia, trauma or seizures, infarcts, and certain chronic neurodegenerative diseases including Alzheimer's disease and PD.

Assays for measuring cell apoptosis are known to the skilled artisan. Apoptotic cells are characterized by characteristic morphological changes; including chromatin condensation, cell shrinkage and membrane blebbing, which can be clearly observed using light microscopy. The biochemical features of apoptosis include DNA fragmentation, protein cleavage at specific locations, increased mitochondrial membrane permeability, and the appearance of phosphatidylserine on the cell membrane surface. Assays for apoptosis are known in the art. Exemplary assays include TUNEL (Terminal deoxynucleotidyl Transferase Biotin-dUTP Nick End Labeling) assays, caspase activity (specifically caspase-3) assays, and assays for fas-ligand and annexin V. Commercially available products for detecting apoptosis include, for example, ApoONE® Homogeneous Caspase-3/7 Assay, FragEL TUNEL kit (ONCOGENE RESEARCH PRODUCTS, San Diego, Calif.), the ApoBrdU DNA Fragmentation Assay (BIOVISION, Mountain View, Calif.), and the Quick Apoptotic DNA Ladder Detection Kit (BIOVISION, Mountain View, Calif.).

Clinical Methods

In some embodiments, methods of the disclosure are used to diagnose, theranose, prognose, and/or determine treatment efficacy for a subject. The term "subject" is intended to include organisms, e.g., prokaryotes and eukaryotes, which are capable of suffering from or afflicted with a disease, disorder or condition associated with the activity of a protein kinase. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from PD, similar forms of Parkinsonism, and synucleopathies involving Lewy body neurodegeneration. In another embodiment, the subject is a cell.

The term "treat," "treated," "treating" or "treatment" includes the diminishment, amelioration, or alleviation of at least one symptom associated with or caused by the state, disorder or disease being treated, e.g., PD, similar forms of Parkinsonism, and synucleopathies involving Lewy body neurodegeneration. In certain embodiments, the treatment comprises the induction of PD or a PD-associated disorder, followed by the activation of the compound of the invention, which would in turn diminish or alleviate at least one symptom associated or caused by the PD or a PD-associated disorder being treated. Treatment can be diminishment of one or several symptoms of a disorder or complete eradication of a disorder.

Nonlimiting examples of neurodegenerative disease that may be diagnosed or prognosed by the disclosed methods include Alexander disease, Alper's disease, Alzheimer's disease, Amyotrophic lateral sclerosis, Ataxia telangiectasia, Batten disease (also known as Spielmeyer-Vogt-Sjogren-Batten disease), Binswanger's disease, Bovine spongiform encephalopathy (BSE), Canavan disease, Cockayne syndrome, Corticobasal degeneration, Creutzfeldt-Jakob disease, Huntingtons disease, HIV- or AIDS-associated dementia, Kennedy's disease, Krabbe disease, Lewy body dementia, Machado-Joseph disease (Spinocerebellar ataxia type 3), Multiple sclerosis, Multiple System Atrophy, Myasthenia gravis, sporadic Parkinson's disease, autosomal recessive early-onset Parkinson's disease, Pelizaeus-Merzbacher Disease, Pick's disease, Primary lateral sclerosis, Refsum's disease, Sandhoff disease, Schilder's disease, Schizophrenia, Spielmeyer-VogtSjogren-Batten disease (also known as Batten disease), Spinocerebellar ataxia (multiple types with varying characteristics), Spinal muscular atrophy, Steele-RichardsonOlszewski disease, Stroke, Tabes dorsalis, Angelman syndrome, Autism, Fetal Alcohol syndrome, Fragile X syndrome, Tourette's syndrome, Prader-Willi syndrome, Sex Chromosome Aneuploidy in Males and in Females, William's syndrome, Smith-Magenis syndrome, 22q Deletion, and any combination thereof

EXAMPLES

Example 1

Assaying Phosphorylation Status of LRRK2

14 different fibroblast lines heterozygous for G2019S were obtained, of which three lines were derived from unaffected carriers, three were from patients homozygous for G2019S and 15 were idiopathic lines from age and gender matched controls. iPSC lines were successfully derived using a retroviral system with four factors (OCT4, KLF4, SOX2, cMYC). These lines were then characterized for pluripotency, differentiation potential, silencing of transgenes, and were karyotypically normal and formed teratoma in SCID mice. A total of 56 fibroblast cells lines were selected for iPSC derivation. Patients were ascertained for specific mutations in the SNCA, Parkin, LRRK2, and GBA genes as well as sporadic cases.

Examination of three clonal iPSC lines that were derived by reprogramming fibroblasts from a patient heterozygous for the G2019S mutation showed LRRK2 detection. Using a validated antibody raised against a C' peptide of LRRK2 (Sheep ?LRRK2 aa2498-2513 S374C16), and using the established LRRK2 expressing cell line Swiss 3T3 as a positive control, LRRK2 was found to be expressed in these IPSC clones. Therefore, this system provides a useful patient derived model for LRRK2-based Parkinson's diseases and allows for studying LRRK2 using pertinent, patient derived cells.

Figure 4:
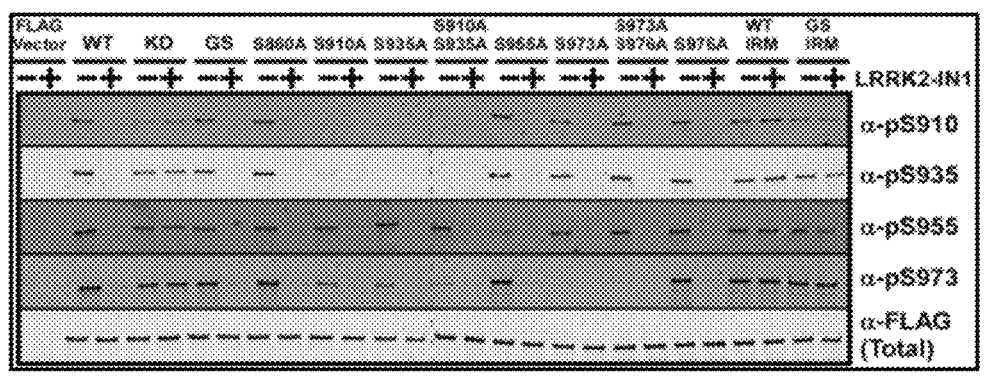
FIG. 4 shows Western blot analysis of LRRK2 N' phosphorylation sites.

Full length, FLAG tagged, wild-type or mutant LRRK2 (as indicated in FIG. 4) was expressed from a stable/inducible locus of HEK293 T-Rex cells (Invitrogen). The data show that the antibodies are phospho-specific and reveal that serines 955 and 973 are regulated similarly to serines 910 and 935. Phosphorylation of serines 955 and 973 in the kinase dead and in the inhibitor resistant mutant samples indicated that these are not autophosphorylation events and that the LRRK2-IN1 inhibitor effects are specific to LRRK2. Additionally, quantitation of these results using the Odyssey system revealed that serine 973 is modified in a manner dependent on phosphorylation of serines 910 and 935. This indicates that phosphorylation of Serines 973, 910 and 935 are interrelated and dependent on LRRK2 kinase activity.

Example 2

Expression of LRRK2 in IPSCs

Figure 5:
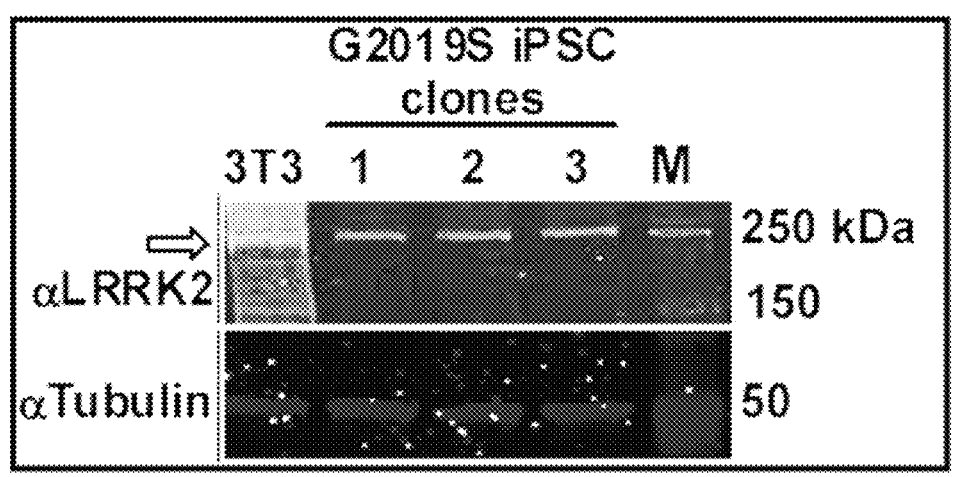
FIG. 5 is a Western blot showing expression of LRRK2 in iPS cells.

Equal amounts of cell lysates from iPSCs derived from patients carrying the G2019S mutation in LRRK2 as well as Swiss 3T3 cells were immunoblotted with anti-LRRK2 (upper) and anti-tubulin antibodies (lower). Three different iPSC clones were used, and are indicated by the numbers 1, 2, and 3 in FIG. 5. Blots were visualized on a LI-COR Odyssey scanner, and the arrow indicates migration of LRRK2. Tubulin staining indicates equal loading of cell lysates, and the band indicated by the arrow shows detection of LRRK2. A list of anti-LRRK2 and anti-phoshpo-LRRK2 is displayed in FIG. 8.

Example 3

Figure 6:
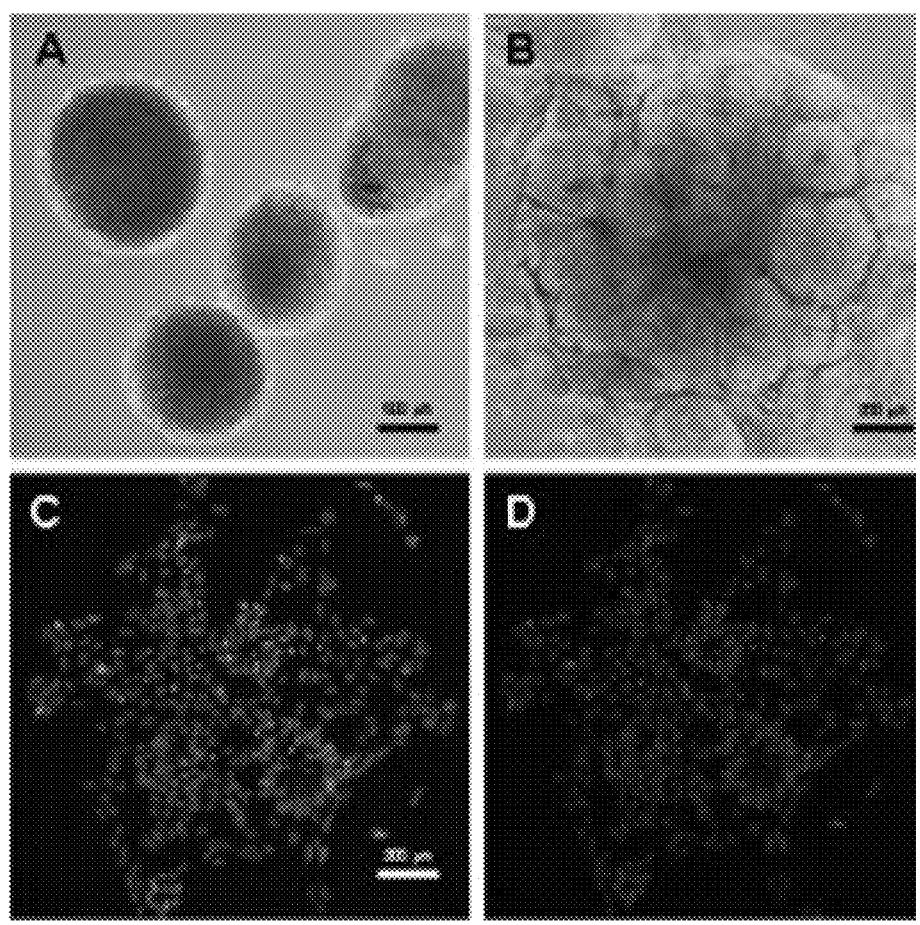
FIG. 6 shows brightfield and immunofluorescence microscopy of neuronal differentiation in culture, including A) embryoid bodies, B) neuronal rosettes, C) Neuronal rosettes immunostained against Pax6, D) Hoechst counterstain.
Figure 7:
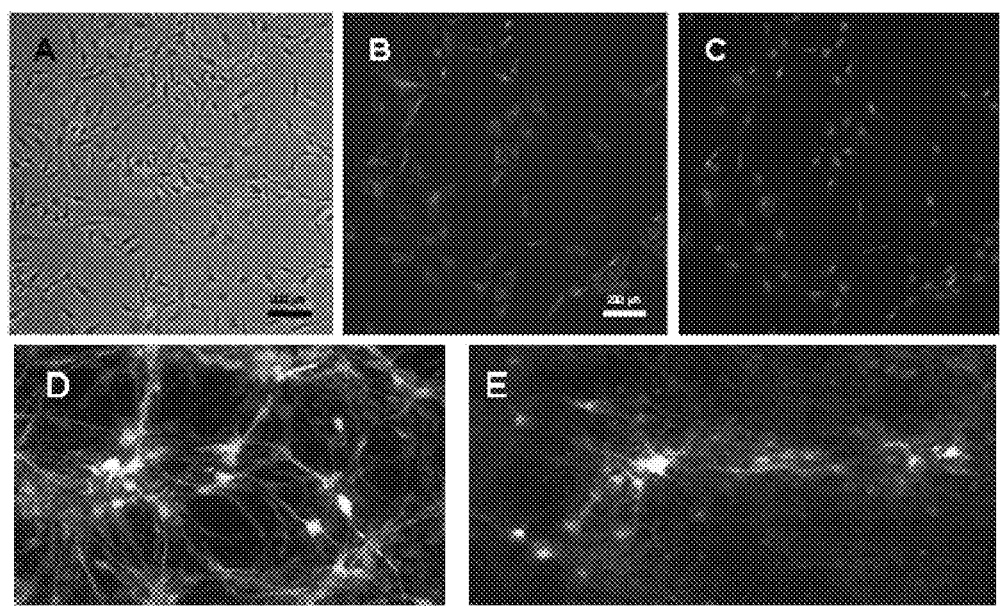
FIG. 7 shows microscopy of neuronal stem cells, including A) phase contrast image of NSCs, B) NSC immunostained against Nestin, C) NSC stained with Sox1, D) differentiated neurons at day 30 stained with gamma-tubulin type III and costain for TH, and E) neurons stained for alpha synuclein and co-stained with TH.

Neuronal Differentiation of iPSC Lines and Evolving Functional PD Related Phenotype A neuronal differentiation protocol was optimized for obtaining patients-derived iPSCs. The employed technique used embryoid body formation (4 days) followed by attachment of embryoid bodies (6-8 days) (FIG. 6A) and isolation of neuronal rosettes expressing Pax6 (FIG. 6B and C). The cells were expanded as neural stem cells (NSCs) expressing Nestin and Sox 1 (FIG. 7A-C). The NSCs can be passaged and cryopreserved. For dopaminergic differentiation the NSCs were cultured in Neurobasal medium supplemented with sonic hedgehog (Shh) (200 ng/ml) and FGF8 50 ng/ml for 10 days followed by withdrawal of Shh and FGF8 and replacement of BDNF (20 ng/ml), GDNF (20 ng/ml), and dcAMP (1 mM) for 20-25 days. After 30 days, cells showed a high yield of gamma-tubulin type III, a marker for an early neuronal phenotype, and showed expression of tyrosine hydroxylase (TH) (FIG. 7D). Co-stain of tyrosine hydroxylase (TH) was also detected in 15-20% of the cells as well as a high yield of microtubule associated protein 2 (MAP2), a postmitotic mature neuronal marker (FIG. 7E). These cells were further characterized for other specific mDA markers (i.e.Pitx3, Nun-1, Lmx1A, AADC, VMAT-2 and Girk2). This indicates a high proportion of final neuronal content for assaying LRRK2. By representing a genetic background that is important for the study of LRRK2, these differentiated cells most closely approximate the disease state.

Example 4

Testing of LRRK2 Assay Probes for use in PLA

PLAs of the disclosure are utilized to detect LRRK2 in differentiated DA neurons that may be generated by iPSC lines derived from subjects with or without Parkinson's disease. A matrix experiment is used to test LRRK2 Taqman Assay Probes for use in PLA. An example matrix is shown in FIG. 9, where labeling of biotin antibody with Oligo A or B is assumed to yield equal activity in the assay. The number of combinations to be tested can be determined by the equation: $(n2-n)/2+$(# of phospho-antibodies, pAb). In the example shown, n=9 and the total number of reactions equals 42. The non-redundant combinations are shown in green, while the pAbs (ie. 3, 4, 5, 6, 7 and 8—in blue) are tested against each other. Following testing, the LRRK2 Assay Probes can be used to detect LRRK2 in differentiated DA neurons.

Example 5

Assay for Intrinsic Kinase Activity of LRRK2 in iPSCs

Using iPSCs derived from subjects with the LRRK2 G2019S genotype, intrinsic kinase activity of LRRK2 can be assessed. LRRK2 from large cultures of iPS cells can be immunoprecipitated using anti-LRRK2 antibodies proven to be able to immunoprecipitate endogenous LRRK2. Immune complexes are assayed for kinase activity against the Nictide peptide substrate, and activity is referenced to control IgG.

Example 6

Assaying LRRK2 Phosphosites as Indicators of LRRK2 Activity

Validated reagents were generated that are capable of detecting phosphorylation events on LRRK2, namely Serines910/935/955/973, which are all regulated by LRRK2 kinase activity. These reagents are used to examine the phosphorylation status of LRRK2 Serines910/935/955/973 in iPSCs. For these experiments, two subjects can be investigated per genotype of control, heterozygous (+/G2019S) and homozygous (G2019S/G2019S), with two iPSC clones per genotype of each subject. This yields 4 distinct data points per genotype. For each experiment, parallel cultures are assayed where each culture is treated with the LRRK2 inhibitor at 1 uM, a concentration shown to completely inhibit LRRK2 feedback phosphorylation. Parallel cultures of T-REx LRRK2 cell lines expressing FLAG or GFP tagged LRRK2 (cell lines we have in hand) serve as positive controls and cultures treated with LRRK2-IN1 inhibitor serve as negative controls.

LRRK2 phospho-specific antibodies are used in a variety of assays to indicate LRRK2 activity, including immunoblots, immunofluorescence, in situ detection, and in solution detection. These assays are described in A-D below. As with all methods of the disclosure, these assays can be performed usign iPSCs differentiated to neuronal stem cells, iPSC-derived differentiated DA neurons, and parallel cultures treated with LRRK2-IN1 or another LRRK2 inhibitor to induce loss of LRRK2 phosphorylation.

A) Immunoblots and in Cell Western Assays in iPSCs or NSCs iPSCs are liberated from the mouse embryonic fibroblast feeder sublayer using collagenase. Lysates of iPSCs are immunoblotted with one of the total antibodies listed in FIG. 8 and phosphorylation of Serines910/935/955/973 is assessed with the rabbit phospho-antibodies listed.

B) Immunofluorescence Microscopy

Phosphoantibody reagents may be applied to higher resolution and spatial analysis through the use of immunofluorescence microscopy. NSCs are cultured in glass bottom culture dishes and conditions are established for detection of LRRK2 and its phosphorylated species using antibodies of the disclosure. Differentiated cultures can also be investigated, in culture using similar glass bottom chamber slides. Antibody reactions are visualized by fluorescence microscopy, providing data on spatial differences in LRRK2 localization. As a control, T-REx cell lines are also assayed.

C) In Situ Detection of Endogenous LRRK2 or Phosphorylated LRRK2

Utilizing two different antibodies to detect a single antigen adds a layer of specificity to the PLA. Specific detection methodologies for detection of LRRK2 are developed using an array of LRRK2 antibodies. Using pairs of antibodies directed against two epitopes of LRRK2 (e.g. MJFF rabbit anti-LRRK2 & Sheep anti-LRRK2 100-500) and secondary antibody reagents from Duolink as the PLA probes, it is possible to establish the detection of LRRK2 in situ or in NSCs derived from iPSCs using fluorescence microscopy. NSCs can serve as a starting point. For controls for amplification, 293 T-REx cells expressing a control protein or LRRK2 in the uninduced and induced state are used. T-REx cells expressing a control cell and the uninduced LRRK2 expressing cells serve as controls for no amplification (or low levels of detection), while T-REx cells expressing LRRK2 serve as positive control for detection of human LRRK2.

Similar techniques are used to detect phosphorylated LRRK2 in situ. Other antibody pairs are employed to investigate the phosphorylation status of LRRK2, e.g. Sheep anti-LRRK2 100-500 in combination with the Rabbit anti-LRRK2 phosphoSerines 910/935/955/973 antibodies.

D) Detection of Endogenous and Phosphorylated LRRK2 in Solution.

Another application of the PLA to detect targets in solution employs similar principles but relies on rtPCR detection of the ligated proximal probes. This amplification of signal is detected by fluorometric PCR instrumentation. In these experiments, iPSCs or NSCs are used as source material for detection and probe sets are designed to detect total LRRK2 as well as modified LRRK2.

Example 7

Application of Proximity Ligation Assays to detect LRRK2 in Differentiated DA Neurons and/or Differentiated Dopaminergic Neurons Immunofluorescence visualization of LRRK2 and its modifications can validate PLA data of LRRK2 expression and phosphorylation. Furthermore, increased sensitivity of PLA allows for a larger dynamic range and higher signal to noise ratio for assays. PLA is performed using methods of the invention in situ for LRRK2 expression as well as for LRRK2 phosphorylation. TH counterstain is used to confirm DA neuron expression.

Example 8

Functional Studies of LRRK2 Activity

Using assays to detect LRRK2 as well as its phosphoforms in differentiated DA neurons, functional aspects can be addressed. The effect of LRRK2 inhibitor treatment on a G2019S induced phenotype can be examined, as can the effect of LRRK2 activity on neuron autophagy, differentiation, and/or survival.

These roles of LRRK2 can be evaluated in controls versus disease models using, for example, iPSC clones for control, +/G2019S and G2019S homozygous and LRRK2 inhibitor to determine how long-term pharmacological inhibition of LRRK2 impacts the differentiation of iPSCs to the DA neuronal lineage. For the persistent exposure regimen, cells are treated with 1 uM LRRK2-IN1 from the early stages of differentiation, formation; at the neural progenitor stage; and at day 5, 10, 15, 20, 25, and 30. During the differentiation process, media is changed every other day; at these times, LRRK2-IN1 is replenished in the culture medium. Differences between genotypes of cells can be examined as well as between cultures exposed to inhibitor or not. Morphological changes like neuritic outgrowth can be compared between the cultures and with DMSO vehicle control. Neuronal architecture is followed using NIH Image J software, and DA neuronal markers expression is monitored. Using the iPSCs as models of existing TH neurons with mutant LRRK2 background, the effect of LRRK2 inhibitor treatment on neuronal survival can be studied.

Autophagy is another functional pathway that can be studied with respect to altered LRRK2 activity.
Wild-type and mutant LRRK2 genotype can be studied for induction of autophagy or autophagic flux using multiple known methodologies. Induction of autophagy is accompanied by the accumulation of LC3 puncta in the cytoplasm of cells and can be easily visualized by immunofluorescence microscopy with commercially available antibodies. Comparing control lines versus LRRK2 mutant lines, it is possible to evaluate the number of endogenous LC3 puncta per cell using computer software such as NIH ImageJ or WatershedCounting3D. If mutant LRRK2 induces autophagy, these puncta should be more prevalent in the mutant lines and be potentially abrogated by LRRK2-IN1 treatment. Inducers of autophagy (nutrient starvation, mTORC1 inhibitors) can also be tested in these models to serve as positive controls for the assay, as well as evaluate whether altered LRRK2 kinase activity can negatively affect the onset of autophagy. A second measure of autophagy that is crucial to appropriate evaluation of LC3 puncta data is autophagic flux, which reveals the convergence of autophagic compartments with functional degradative compartments. Otherwise, LC3 accumulation could misinterpreted as an increase in the onset of autophagy instead of a disruption downstream of autophagy induction. A quenching assay can be used to detect the convergence of autophagic compartments with the late lysosomal compartments. Here, dequenched BSA is heavily labeled with BODIPY TR-X dye, resulting in self quenching of the fluorophore. This is incubated in the culture medium and will accumulate in lysosomes, where upon degradation, the fluorophore becomes fluorescent and indicative of functional lysosomes. Co-localization with LC3 is indicative of functional fusion of autophagic compartments with degradative compartments. The accumulation of p62, which should not occur if autophagy is active, can also be measured. Another parameter used to study autophagy is LC3 localization. A tandem green and red fluorescent protein-conjugated to LC3 can be used to detect LC3 localization. GFP-RFP-LC3 proteins localize to the autophagosome, which fuses with the lysosome to form the autolysosome, where degradation of cellular components occurs. Appropriate progression of autophagy brings the GFP-RFP-LC3 protein to the autolysosome where the GFP signal is quenched by the low pH. Therefore colocalization of RFP and GFP indicates no autophagy, and red fluorescence after autophagy induction indicates faithful maturation of the autophagosome. NSCs can be generated that stably express this fusion protein using lentiviral methods or standard electroporation and stable cell cloning. Following differentiation, these models can be subjected to the above analyses to assess the full impact of mutant LRRK2 on neuronal survival and autophagy as well as the efficacy of LRRK2-IN1 treatment.

Example 9

Forced Proximity Probe (FPP) Test and Evaluation of PLA probes Using Recombinant Proteins Antibodies are labeled with biotin in batches of 5 at a time using 50 ug of antibody, using standard protocols. Biotin-labeled antibodies are then conjugated, in separate batches, with streptavidin-oligo probes A and B. One reason for utilizing multiple total LRRK2 antibodies and multiple different phosphoantibodies is that these reagents may lose antigen reactivity via the biotin labeling process. The multiple antibodies choices are designed to allow for differential sensitivities after labeling as well as to account for potential loss of reactivity. Employing antibodies that recognize multiple epitopes of LRRK2 increases the probability of defining antibody pairs that will faithfully recognize the protein.

Figure 10:
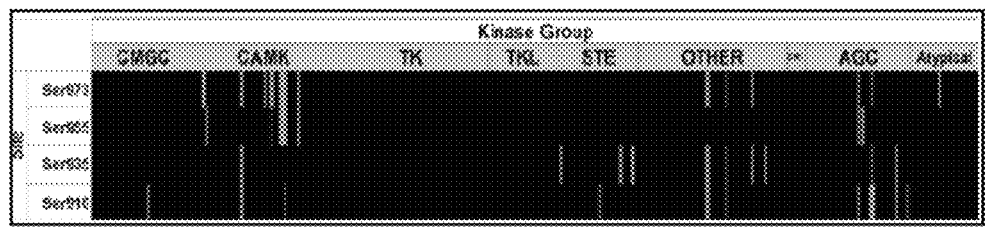
FIG. 10 shows distribution of kinases across the kinome that modify the indicated residues.

After biotin labeling and oligo conjugation, antibodies are tested in the FPP test. The FPP test is a crucial evaluation of the suitability of labeled antibodies to be employed in the PLA. In this test, antibodies are evaluated for their efficacy, etc. PLA probe antibodies that pass the FPP test are evaluated for their ability to detect total LRRK2 and phosphoLRRK2 when presented as recombinant proteins. Invitrogen has generated epitope-tagged, full length LRRK2, which will be used for optimization of LRRK2 total protein PLA. For recombinant, phosphorylated LRRK2, multiple kinases capable of modifying LRRK2 Serines 910/935/955/973 were identified. Bacterially expressed, GST tagged LRRK2 800-1300 was used as substrate in a screen of 318 kinases across the kinome. FIG. 10 shows the distribution of kinases capable of modifying LRRK2 serines. In the figure, individual kinases are represented by a single lines. Kinase names are omitted, but kinase groups are indicated.

Example 10

Screening and Confirmation of PLA Probes with Purified LRRK2 and Phosphorylated Recombinant Proteins Using validated PLA antibodies against the epitope tags of the recombinant proteins (GST), target- and phospho-specific LRRK2 Assay Probes are screened in combination with anti-epitope Assay Probe. Eight total LRRK2 Assay Probes tested against each other and the antiepitope probe are described in a matrix shown in FIG. 9. Phospho LRRK2 Assay Probes are tested against the anti-epitope probe and the total LRRK2 probes shown to drive successful TaqMan protein assay results. The best combination of assay probes (including testing the reverse B vs A oligos) is confirmed in a repeat of the TaqMan® Protein Assay.

LRRK2 is known to be associated with 14-3-3 as well as Hsp90. 14-3-3 proteins associate with LRRK2 in a phosphoserine dependent manner and loss of 14-3-3 protein interaction is indicative of inhibited LRRK2 kinase activity or the presence of PD associated mutations that induce cytoplasmic aggregation and loss of 14-3-3 interaction. Hsp90 association with LRRK2 helps maintain LRRK2 stability, as geldanamycin treatment is known to decrease LRRK2 accumulation. For both 14-3-3 and Hsp90, successfully validated total LRRK2 antibodies are tested in combination with 14-3-3 and Hsp90 antibodies. Serial dilution of recombinant LRRK2 Protein Standard is used to determine the limit of detection of the assay for, e.g., the best pair of probes for total LRRK2 and each phospho-LRRK2.

Example 11

LRRK2 Proximity Ligation Assay Validation in Cell Lysates

To transition from recombinant protein assays to cell lysates, the efficacy of the PLA probes to detect recombinant or endogenous LRRK2 is evaluated. Lysates from cells that overexpress LRRK2, either from cells containing GFP-LRRK2 or cells transduced with BacMam LRRK2-GFP, are used to screen the PLA Probes. Lysates are generated using LanthaScreen Lysis buffer (Invitrogen). HEK293 T-REx™ cells expressing amino-terminal GFP tagged WT, G2019S, D2017A, R1441C/G, I2020T, S910A, S935A, S910A/S935A, S955A and S973A LRRK2 are employed. Additionally, lysates from the dopaminergic cell line SH-SY5Y and/or cells transduced with BacMam carboxy-terminal GFP tagged full length LRRK2-GFP are used. Using two sources of cell lysate (T-REx™ vs. BacMam) lends insight into the effects of amino- vs. carboxy-terminal fusions of GFP with LRRK2. Moreover, the phosphorylation status of each LRRK2 construct is evaluated, thus yielding valuable confirmative information on the phosphorylation status of these mutant proteins.

PLA is then applied to cell lines that endogenously express LRRK2. The amount of total LRRK2 target protein and the phosphorylation status is evaluated and compared across different cell lines. Examples of cell lines that endogenously express LRRK2 are Raw macrophages, EBV transformed human lymphocytes and SH-SY5Y cells. A negative control (HEK293 T-REx™ GFP) and positive control (HEK293 T-REx™ GFP-LRRK2) cell lysate are included for comparison.

Example 12

Patient Ascertainment and Peripheral Blood Mononuclear Cell Purification for Application of Validated PLA Probes to Patient Derived Samples An ultimate and crucial application of the PLA validated probes is to assess the phosphorylation status of LRRK2 in patient derived samples. A study group of patients has the following inclusion criteria: Diagnosis of idiopathic PD, no atypical signs of parkinsonism, disease duration 3+ years, current age 55-75 yrs, both genders, Caucasian. The control group consists of age, gender, and ethnicity matched subjects recruited through the Parkinson's Institute which are spouses or other community members. They are not diagnosed with either PD or any other neurodegenerative disorder and have no family history of these diseases. The clinical assessment of all subjects includes a general neurological history and examination, including the modified Unified Parkinson's Disease Rating Scale (UPDRS), Hoehn and Yahr staging, cognitive screening (MOCA), and Brief smell identification test (B-SIT). Diagnostic criteria are applied by using all available information sources (UPDRS ratings, other clinical assessments, medical records). The NINDS criteria, which have integrated the key features of other diagnostic schema (CAPIT47, UK Brain Bank), are used. This clinical assessment is supplemented by detailed structured family histories. A three-generation pedigree and family history provides the necessary information for identifying additional eligible relatives of the family. All data are stored in password protected databases and safety precautions are taken to fulfill protection of any human subject as required by law.

Three 10 ml-heparin blood tubes are collected for the isolation of peripheral blood mononuclear cells using Uni-Sep-MAXI tube (NOVAmed) using standardized percoll based protocol. During sample ascertainment, cells are snap frozen in liquid nitrogen until all samples are collected for analysis. DNA is also collected from a portion of the PBMCs for LRRK2 G2019S genotyping, as well as plasma for future follow-up studies.

Example 13

PLA Detection of LRRK2 in PBMC Lysates

A validated PLA is applied to samples derived from patients to establish a protocol that can be applied to patients treated with LRRK2 inhibitors. PBMCs are lysed in LanthaScreen lysis buffer supplemented with protease and phosphatase inhibitors, aliquoted and snap frozen for repeat analyses. PLA is performed using these cell samples to detect total levels of LRRK2 and assess the phosphorylation of LRRK2 as a putative pharmacodynamic marker.

Example 14

Assaying LRRK2 Dimerization and/or Interactions in Cell Lysates

PLA is performed using lysates from cells that over-express LRRK2 and cells that express endogenous LRRK2 (i.e. SH-SY5Y or Raw macrophages or human lymphoblasts). For the interaction assays, PLA probes for 14-3-3 and Hsp90 interacting proteins (from Aim 1A) are initially tested against full-length recombinant proteins in combination with anti-epitope Assay Probes. These assays are also performed on lysates of cells expressing epitope tagged LRRK2 or endogenous LRRK2. In this way, a PLA for LRRK2:14-3-3 interaction can be established and used as an additional marker of LRRK2 kinase activity inhibition or mutation induced dephosphorylation of Ser910/935. Additionally, since LRRK2 is likely to be constitutively associated with Hsp90, this interaction assay serves as a positive control for protein: protein interactions involving LRRK2.

LRRK2 has been described as a dimer via multiple interaction interfaces. Additionally the dimerization status of LRRK2 changes in the context of altered kinase activity and PD associated mutation. LRRK2 total protein probes are used to develop a LRRK2:LRRK2 interaction assay. For dimerization assays, the PLA is performed using various total LRRK2 Assay Probes—either the same anti-LRRK2 mAb or pAb labeled with Oligo A and B, or the best mAb labeled with Oligo A and the best pAb labeled with Oligo B. Cells useful for these assays are HEK293 T-REx™ cells expressing aminoterminal GFP tagged WT, G2019S, D2017A, R1441C/G, 12020T treated with or without LRRK2-IN1 as an initial source of LRRK2 enzyme.

Example 15

Utilization of the Novel Nictide Substrate Sequence, in Silico Prediction, and Peptide Substrate Libraries to Identify LRRK2 Kinase Substrates An antibody raised against the phospho-Nictide sequence is used to retrieve immunoreactive proteins from cell lysates (Swiss 3T3 or Raw macrophages), which are then be tested for their ability to serve as substrates of LRRK2. Pre-immune antibody serves as a control for immunoprecipitation and cells pretreated with H-1152 or sunitinib to prevent LRRK2 phosphorylation of proteins serve as control lysates which do not contain LRRK2 phosphorylated proteins. Immunoprecipitates are resolved by SDS-PAGE and stained with colloidal blue. Proteins that appear to preferentially associate with the anti-Nictide antibody from untreated lysates are identified by mass-spectrometry and considered candidate substrate proteins. For in silico prediction of substrates, empirical data derived from the Positional Scanning Peptide Library screen, from which the Nictide optimal peptide substrate sequence for LRRK2 was derived, is utilized to interrogate sequence databases for proteins that may serve as potential LRRK2 substrates Utilizing kinase screening services of Jerini Peptide Technologies GMBH (Berlin, Germany) with recombinant LRRK2, LRRK2 substrate sequence preference can be weighed against novel substrate peptides revealed from the screen to reveal likely substrate candidate substrates. A panel of 1600 peptides representing kinase activation sites can be screened, as well as a panel of 2304 peptides representing annotated phosphosites. Substrates identified in the screen are referenced with LRRK2 substrate sequence preference and likely substrates are prioritized. This also provides a basis for substrate preference validation.

Example 16

Identification of Kinases or Phosphatases that Modify LRRK2 at Ser910/Ser935

Phosphorylation of Ser910 and Ser935 on LRRK2 has been shown to mediate binding to 14-3-3 on LRRK2, is dependent on LRRK2 kinase activity and regulates subcellular localization. Monitoring these was shown to be a useful means to evaluate LRRK2 inhibitors in cell culture model systems. The kinase activity responsible for modification of Ser910 and Ser935 is not an autophosphorylation event and is likely through LRRK2 mediated positive regulation of a kinase or negative regulation of a phosphatase. Therefore, a prime source to find a likely substrate for LRRK2 is to elucidate the enzymes responsible for modification of these sites. Multiple complementary techniques can be employed to identify the kinase responsible for these modifications: pharmacological inhibition of the kinase, phosphorylation of LRRK2 with a panel of candidate kinases, co-immunopurification as well as a siRNA screen to define the phosphatase that regulates Ser910/Ser935.

Using cells expressing the LRRK2 dependent kinase endogenously, either non-selective or specific kinase inhibitors are administered against upstream kinases (e.g. inhibition of PI3K/mTOR) and kinases that have known preferences for basic residues at the −3 and −4 position relative to the phosphorylation site, in order to narrow the possible kinase(s) responsible for the modification of LRRK2 Ser910/Ser935. The LRRK2 Ser910/Ser935 phosphorylation sites were subjected to database searches using the netphorest algorithms which include most kinase substrate recognition sequences to help direct the search of the upstream kinase.

LRRK2 kinase-inactive protein is still modified at Ser910/Ser935, albeit at a lower level than active LRRK2. This most likely represents a basal level of modification of these sites in the absence of LRRK2 activation of the kinase. Therefore, as an alternative approach, to avoid LRRK2 kinase activity propagating the feedback of kinase activity on Ser910/935, inhibitors are evaluated using kinase inactive LRRK2 as a substrate; therefore the screen can be repeated in this experimental background. For these experiments, cells expressing recombinant, kinase-inactive LRRK2 (T-REx system) are treated with the test inhibitor and total LRRK2 will be immunoprecipitated, then immunoblotted with anti-phosphoserine 910 (pSer910) and anti-phosphoserine 935 (pSer935) antibodies. Kinases targeted by the tested inhibitors that suppress modification of Ser910 and Ser935 are classified as candidate substrates of LRRK2. Inhibitors are tested to ensure that they do not inhibit LRRK2 directly by testing candidate compounds against recombinant LRRK2 in vitro. Potential substrate kinases are also considered putative upstream kinases for LRRK2 Ser910/Ser935.

An LRRK2 kinase or phosphatase can also be identified using co-immunoprecipitation analysis. The amino-terminus (amino acids 1-1300) and/or the 780-1300 domain can be used as bait. Using cells expressing either GFP, or GFP fused to amino acids 1-1300 or 780-1300, anti-GFP affmity chromatography is performed using ChromoTek nanotrap GFP-Binder beads. Proteins that specifically are enriched in these pull-downs can be identified by mass-spectrometry and considered candidate substrates of LRRK2. Additionally, utilization of these isolated domains may increase likelihood of identifying the interacting partners, as analysis of these domains in isolation may increase the 'specific activity' of interaction. To further increase the likelihood of identifying the LRRK2 kinase or phosphatase, in these experiments and other co-immunoprecipitation experiments a reversible chemical crosslinking agent can be added to the lysis buffers in order to increase the probability of capturing more transient associations. The phosphorylation sites in question are close to the leucine rich repeat domain, which could serve as a protein:protein interaction domain that bridges the upstream enzyme to the sites of modification and it may therefore be possible to co-precipitate the modifying enzymes that regulate these sites.

In vitro, phosphatases may more readily dephosphorylate non-physiological substrates. Reverse genetics can be used to elucidate the phosphatase that dephosphorylates Ser910/Ser935, by using a siRNA library targeted against the phosphatase complement of the human genome. The T-REx expression system can be employed to express GFP tagged LRRK2. LRRK2 is localized in a diffuse, cytoplasmic pattern. In the presence of Inhibitor, LRRK2 is found to be dephosphorylated and in cytoplasmic aggregates. For the screen, LRRK2 dephosporylation is assayed immunologically (loss of signal) or by the induction of GFP-LRRK2 aggregates, two solid readouts of LRRK2 modification. First, cells are administered the phosphatase targeting siRNAs, followed by acute, 90 minute, LRRK2 inhibitor treatment. If the phosphatase that mediates the dephosphorylation of LRRK2 is repressed, then LRRK2 inhibition should not result in dephosphorylation and aggregation. GFP fluorescence can serve as an internal control for LRRK2 expression and Ser910Ala and Ser935Ala substitution mutants can be used as controls for non phosphorylated LRRK2. Positive hits of the screen are validated by targeted siRNA depletion of the phosphatase, followed by biochemical validation that it is a substrate of LRRK2. Utility of this screen is validated by utilizing broad spectrum phosphatase inhibitors such as calicylin A and okadaic acid as hallmarks of phosphatase inhibition.

Example 17

Biochemical and Chromatographic Purification of the LRRK2 Kinase

Since cells expressing LRRK2 contain the kinase that modifies Ser910/Ser935, chromatographic techniques are useful to purify the kinase from cell lysates and/or brain lysates. Multiple methods of cell lysis can be employed in order to preserve the kinase activity, namely mechanical, isotonic disruption of cells versus detergent based extraction of cells, which may easily disrupt a potential signaling complex (such as the mTOR complex being disrupted by Triton X-10019). The Ser910/Ser935 kinase activity can be enriched by column chromatography, where cell lysates are fractionated first by differential centrifugation (in the case of mechanical disruption) and then by ion exchange column chromatography. Serine910/935 kinase activity is monitored across the column fractions by using portions of the fractions as the source of kinase in a kinase assay with recombinant LRRK2 as a source of substrate and monitoring for specific modification of 910/935 by immunoblot analysis. Fractions containing the activity are further enriched until it can be identified by mass spectrometry.

Example 18

Mechanistic Dissection of LRRK2 Phosphorylation

Reagents can be generated to detect phosphosphorylation of serines 860, 955 and 973/976 and determine if they are responsive to LRRK2 kinase activity. To understand the role of these sites in LRRK2 biology, phosphospecific antibodies are raised against these phosphosites. The ability of these sites to be phosphorylated in response to LRRK2 activity will be examined as the 910 and 935 sites have been. The phosphorylation status of these sites will also be analyzed in the PD associated mutations and the impact on LRRK2 stability/aggregation will be assessed.

The carboxy-terminal domain of LRRK2 is necessary for kinase activity, and a detailed study of this domain can help to understand the role the carboxy terminus plays in regulating LRRK2. For example, the ability of this domain to reconstitute an active complex in trans can be determined by transfection of an LRRK2 variant lacking these 8 amino acids (CΔ8), into cells stably expressing the carboxy terminal domain with or without the carboxy terminal 8 amino acids. After co-expression, activity of the LRRK2 CΔ8 will be assessed by ability to phosphorylate Nictide in immunoprecipitation kinase assays. To determine if the carboxy terminal 8 amino acids can mediate this regulation of LRRK2 alone, lysates of cells expressing wild type or CΔ8 LRRK2 will be prepared in the presence of excess CΔ8 peptide encompassing the last eight amino acids; a non related peptide of similar length will used as a control. If kinase activity is modulated by this peptide alone it could inhibit wild type or activate CΔ8. If wild type LRRK2 is inhibited, it will indicate that this peptide can compete for a crucial binding site on the activating protein, precluding association and activation of the kinase domain. If the CΔ8 is activated by addition of the peptide, it will indicate that the C' domain acts as an autoregulatory domain conferring activity to the protein. Additionally, this peptide can be added directly to an immunoprecipitation kinase assay LRRK2 (wildtype versus CΔ8) to determine if it can activate or inhibit the protein in isolation. If this peptide does modulate kinase activity of LRRK2, mutational analysis of the peptide will be carried out to determine the necessary residues that confer or inhibit activity.

The carboxy terminus may interact with a protein that confers activity to LRRK2. These proteins can be identified by co-immunoprecipitation analysis using the carboxy terminal domain of LRRK2 fused to GFP, with and without the last eight amino acids to define specificity. A reversible chemical crosslinking agent to the lysis buffers can increase the probability of capturing more transient associations. Candidate substrates from Nictide based identifications can be prioritized based on similarity to the Nictide sequence, gene expression patterns and published phosphosites databases (e.g. phosphoELM and phosida). To test the ability of LRRK2 to phosphorylate candidate proteins, cDNAs of candidate proteins are cloned and recombinant protein expressed in prokaryotic or eukaryotic cells. It can then be tested whether recombinant wild type and G2019S LRRK2, but not kinase inactive LRRK2 can phosphorylate these substrates. As a control equivalent molar concentrations of the C-terminal domain of moesin, which is efficiently phosphorylated in vitro by LRRK2 at Thr558, can be used. A physiological LRRK2 substrate would be phosphorylated by LRRK2 at least as efficiently as moesin.

When substrate(s) are verified in vitro, site(s) can be mapped using a combination of mutational and phosphoproteomic techniques commonly used in the field of signaling. These include mass-spectrometric identification of phosphopeptides or isolation of the phosphorylated peptide by enzymatic digest followed by HPLC and direct sequencing by Edman degradation or mass spectrometry. Phosphospecific antibodies can be used to establish whether the same sites on the substrate are phosphorylated in cells, and how this phosphorylation is affected by overexpression of wild type or G2019S or kinase-inactive LRRK2, and if administration of LRRK2 inhibitors blocks phosphorylation at these sites. siRNA knockdown of endogenous LRRK2 in Swiss3T3 or Raw cells can be tested for impact on phosphorylation of the identified LRRK2 substrate.

Example 19

Assaying LRRK2 Activity in Human Biological Samples

A) Establishing a Method for Directly Assaying LRRK2 in Blood Samples.

Understanding if these assays will work in patient samples is crucial to including them as a readout of LRRK2 inhibition as part of a clinical trial protocol. The Ser910/Ser935 phosphorylation assays can be applied to lymphocytes purified from blood samples to establish the assay. Antibody based and density centrifugation based lymphocyte purification methods can be compared for ease and rapidity in cell isolation. Cells are rapidly lysed and Ser910/935 phosphorylation is determined by immunoprecipitation of LRRK2 followed by immunoblot with Ser910/Ser935 antibodies. Additionally, LRRK2 immunoprecipitation kinase assays can be applied to these samples.

B.) Application of LRRK2 Activity Assays to PD Patient Derived Samples Adapted to Cell Culture Model Systems.

LRRK2 kinase activity and phosphospecific antibody based readouts of LRRK2 activity can be applied to Parkinson's disease patient samples that have been adapted to cell culture model systems. These systems are vital to establishing drug efficacy or toxicity for clinical trials. Evaluated samples can include control, as well as mutation induced PD (LRRK2 G2019S or other genotype, alpha-synuclein multiplication, and also early onset PD and GBA mutation, all of which are available). From these disease backgrounds, skin fibroblasts, skin fibroblasts induced to be iPS cells and lymphocytes can be examined LRRK2 activity can be measured in fibroblasts and in lymphocytes, indicating that these could be good model systems to perform initial biochemical validation of LRRK2 responsiveness to novel inhibitors or whether newly identified substrates are responsive to LRRK2 activating mutation. A large library of tissue samples (particularly fibroblasts) from LRRK2 patients is available, including both heterozygous and monozygous patients. These cell systems are initially characterized by determining the phosphorylation status of Ser910/Ser935, or other phosphorylation sites. The specific kinase activity of endogenous, wild type LRRK2 versus LRRK2 from samples harboring mutations is also determined by immunoprecipitation kinase assay against the Nictide substrate. These assays yield insight into the steady state level of LRRK2 activity.

iPS cells derived from PD patients harboring LRRK2 and alpha synuclein mutations can also be tested. These cells continuously replicate and are a regenerative source of mutant LRRK2 model systems. The steady state level activity of LRRK2 can be characterized from these cells in the undifferentiated state, as well as cells differentiated to a neuronal state. An alternate technique of visualizing phospho Ser910/Ser935 can be used, whereby immunofluorescence microscopy of differentiated neurons is employed using phosphospecific antibodies against these sites, to determine a difference in kinase activity between the differentiated and undifferentiated state.

Example 20

Characterization of LRRK2 Stability and Aggregation and Link to Autophagy

Two apparent general classes of PD associated mutations have been observed. One class of mutation affects kinase activity, either positively or negatively. The other confers an increased propensity to aggregate, which is likely to be caused by a reduction in the ability to bind 14-3-3, while not affecting kinase activity in immunoprecipitation kinase assays. Aggregates formed by PD associated mutation can be used to dissect the role of LRRK2 in signaling pathways. The tetracycline regulatable (tetR) system allows for the distinction between aggregates induced by pathogenic mutation when compared to wild type LRRK2 expression. Using the inducible tetR system, potential disruption of constitutive autophagic process may be avoided.

LRRK2 is found in aggregates when examined in the context of certain PD associated mutations, acute pharmacological inhibition and disruption of 14-3-3 binding. Wild type LRRK2 expressing cells are treated with inhibitors of, and siRNAs against a) the ubiquitin-proteasome pathway b) the aggresome formation pathway c) the autophagy pathway and d) cellular chaperone apparatus and are evaluated microscopically for the formation of wild type LRRK2 aggregates. Conversely, cellular factors may facilitate aggregate formation in the context of certain LRRK2 mutations. Cells expressing LRRK2 aggregation prone mutants are screened with siRNAs and drugs for the ability to dissipate the aggregates. PD associated mutations may confer an intrinsic instability to a polypeptide that self associates and therefore possess a higher propensity to aggregate if small protein synthesis imbalances occur. Alternatively, these mutations may disrupt an as yet uncovered interaction with one of these cellular processes which in turn results in a disruption of LRRK2 intracellular localization. Utilizing the Ser910Ala/Ser935Ala mutants, colocalization experiments are conducted to define the components of LRRK2 aggregates.

Components of the cytoskeleton as well as vesicle trafficking pathways can be examined Alternatively, LRRK2 can be immunoprecipitated when expressed as aggregation prone mutations in order to identify by mass spectrometry, novel proteins that preferentially associate with the aggregating LRRK2 versus wild-type LRRK2.

14-3-3 binding to LRRK2 is sensitive to LRRK2 kinase activity; however, the binding of 14-3-3 does not affect protein kinase activity. LRRK2 that is unable to be modified at Ser910 and Ser935 (i.e. Ser910A
and Ser935A) exhibits altered localization compared to wild type. Additionally, acute administration of LRRK2 inhibitors results in the aggregation of LRRK2. It can be determined if overexpression of 14-3-3 suppresses the aggregation of LRRK2 induced by mutation. If over expression of 14-3-3 does relieve the formation of aggregates, a cellular autoprotective mechanism will have been revealed where LRRK2 kinase activity promotes association of a cellular factor that prevents aggregate formation.

Aggregation prone mutations can be screened in the context of a kinase inactive mutation, i.e. R1441G/C/H+D2017A, Y1699C+D2017A, etc., for the tendency to form aggregates. It has been shown that proteinacious aggregates induced by pathogenic mutation in the Huntington protein (polyglutamate expansion HttQ103), the Ataxin1 (polyglutamate expansion AtxQ82) or rhodopsin (P23H mutation) all disrupt the ubiquitinproteasome system (UPS) and cause accumulation of reporters of UPS dependent protein degradation. This UPS monitoring system is applied to cells expressing LRRK2 wild-type or LRRK2 aggregation prone mutations. If LRRK2 aggregation prone mutations induce a global disruption of the UPS, it reveals a pathway of LRRK2 pathogenesis possibly crucial in understanding disease.

Direct assessment of LRRK2 protein:protein interaction with components of the autophagy machinery will be carried out using co-immunoprecipitation analysis. It will be determined whether autophagy components serve as direct kinase substrates of LRRK2 in vitro, and if so, the impact of these modifications exert on their role in the autophagy process will be determined in vivo by employing phosphosite mutants (unphosphorylatable Ala or phosphomimic Glu) and monitoring the effects on constitutive autophagy or on autophagy after induction by starvation or bafilomycin A treatment. Expression of the LRRK2 PD associated mutants, especially ones which induce protein aggregation, will be evaluated for their affect on autophagy by measuring conversion of LC3I to LC3II, effects on p62 levels and formation of LC3 intracellular puncta under normal and autophagy induction conditions in accordance with the guidelines for monitoring autophagy.

LRRK2 is reported to be ubiquitinated by CHIP and this regulates the level of protein stability. It will be assessed whether this is a signal for chaperone mediated autophagy by evaluating whether co-expression of LRRK2 and CHIP, leads to enhanced ubiquitination of LRRK2, increasing interaction or expression of p62, the protein which binds ubiquitinated proteins and LC3 to link with autophagy.

Example 21

Generation of iPSC Lines from Parkinsonian Patients with the LRRK2 G2019S Mutation and Unaffected Mutation-Negative Controls iPS cell lines are derived from PD patients carrying mutations in different PD genes and controls. Fibroblasts have been derived from skin biopsies and banked from 14 patients who are heterozygous for the LRRK2 G2019S mutation. Fibroblast cell lines have been developed from three patients who are homozygotes for the mutation. Using a retroviral system to deliver four genes encoding OCT4, KLF4, SOX2 and cMYC, iPSC lines have been successfully derived from five LRRK2 patients and nine control iPS lines. These lines have been characterized for pluripotency and are karyotypically normal. They are further assessed for teratoma formation and promoter methylation of Oct4 and Nanog.

Example 22

ZFN-Mediated G2019S Allele Disruption in Patient-Derived Fibroblasts

Figure 11:
FIG. 11 shows disruption of the G2019S allele (sequence indicated in A) in B) K562 cells and C) patient-derived fibroblasts.

FIG. 11 shows efficient cleavage of the LRRK2 gene in a pool of patient-derived fibroblasts that were transfected with ZFN. The transfected cell pool was subject to single cell cloning—clones that contain either insertion or deletion at the site of DSB will lose the BsrDI restriction site. Sequencing analysis of 7 such clones revealed 3 clones that contain frameshift mutations of the G2019S allele, thus disrupting the translation of the protein.

Referring to FIG. 11, the asterisk (*) denotes the base change that results in G2019S mutation, ZFN binding sites are underlined. ZFP drives LRRK2 gene modification in K562 cells (B) and patient-derived (G2019S heterozygotes) fibroblasts (C). A 346-bp region encompassing the ZFN cleavage site was PCR-amplified from ZFN-transfected cell pools, generating a mixture of unmodified as well as modified amplicons (derived from NHEJ-mediated imperfect repair of the DNA break); denaturing and reannealing of this mixture results in mismatches between heteroduplexes of the unmodified and modified alleles, which create distortions that are recognized and cleaved by Cel-1 nuclease. The top band represents uncut PCR products, the cleavage products are indicated by #. For patient-derived fibroblasts, * denotes cleavage products resulted from the heteroduplex between wt and unmodified G2019S alleles. The relative intensity of the cleavage products compared with the parental band was quantitated by densitometryis, and provides a measure of the frequency of ZFN-mediated cleavage of the LRRK2 gene that was repaired by NHEJ-—19% in K562 cells and 16% in fibroblasts.

Example 23

Stress Response of Neurons Derived from G2019S and Control Cell Lines

Figure 12:
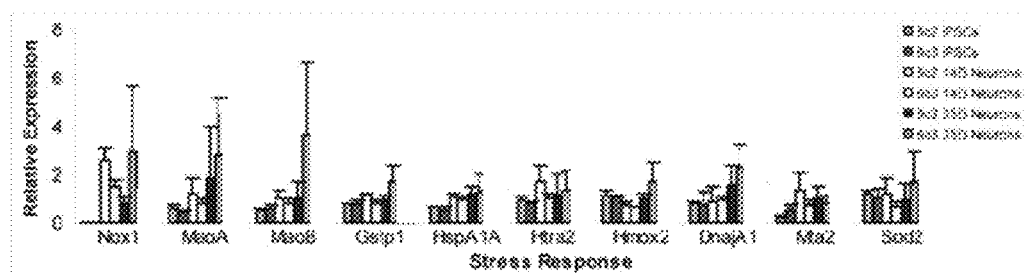
FIG. 12 displays the results of quantitative RT-PCR analysis showing average expression of the indicated stress-response genes in iPS and neurons from G2019S (6c3) and control (5c2) lines. Error bars represent standard deviation of 3+ biological replicates. Expression was normalized to GAPDH, CentB3, Eef1 A.

To further increase the yield of midbrain dopaminergic (mDA) neurons, iPSC-derived neurons are cultured under low oxygen conditions (3-5% oxygen). Referring to FIG. 12, NSCs and TH-positive neurons were derived from normal and LRRK2 positive clonal iPSC lines. These cells were further characterized for other specific mDA markers (i.e. Pitx3, Nurr-1, Lmx1A, AADC, VMAT-2 and Girk2).

Figure 13:
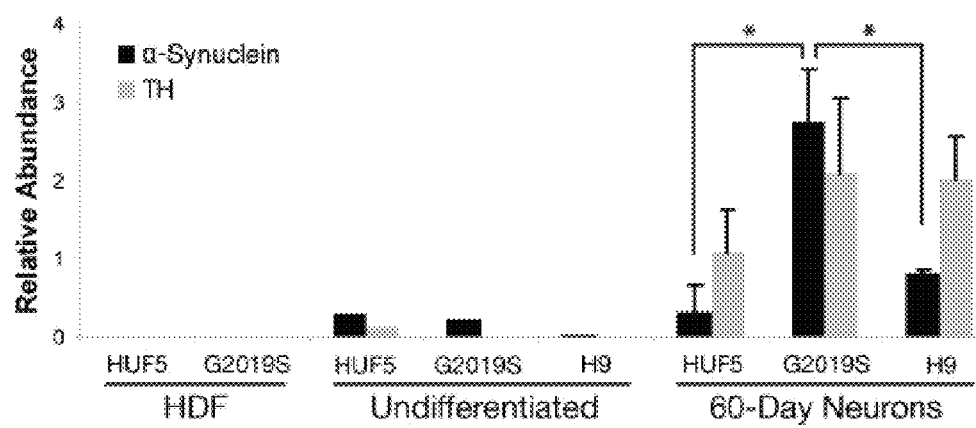
FIG. 13 shows Western blot analysis of alpha-synuclein and TH expression in human dermal fibroblasts (HDF), undifferentiated iPS and neurons at day 60 of a culture protocol, as indicated.

During a time course the mDA neurons from a patient carrying the LRRK2 G2019S on both alleles showed an increase in markers of stress response genes as well as an increase in alpha-synuclein protein expression compared to control lines (FIG. 13) exhibiting an early functional phenotype, both of which could be characteristic of PD pathology Mitochondrial function and lysosomal abnormalities can be investigated in these iPS-derived mDA neurons.

Example 23

Generation of Patient-Derived iPSCs with Corrected or Disrupted LRRK2 G2019S Allele Patient-derived iPS cell lines with corrected or disrupted G2019S allele provide cell models and their corresponding isogenic controls are useful tools. The G2019S allele is disrupted to achieve a functional knockdown, because the G2019S mutation is a gain-of-function mutation and shows an at least a two to three-fold increase in kinase activity due to an increase in reaction rate. Patient-derived iPSCs with corrected or disrupted G2019S allele provide cell models to determine whether the G2019S mutation is necessary for developing PD-related phenotypes, and help to understand the relative contribution of the G2019S to PD phenotype. Correction and disruption of the G2019S mutation is performed in a minimum of two independent iPSC lines derived from the same patient; and the same process is carried out on iPSCs derived from 3 unrelated patients that carry the mutation, providing isogenic cell models for studying the role of G2019S mutation in the context of different genetic backgrounds.

A lead ZFN pair (LRRK2 ZFNs) that cleaves DNA at a site ~20 by upstream of the G2019S mutation has been validated in K562 cells and patient-derived fibroblasts. The DSB introduced by ZFNs can be repaired via HDR or NHEJ-based pathways, resulting in either correction or disruption of the mutant allele.

Plasmids encoding LRRK2 ZFNs, the green fluorescent protein (GFP) and a donor DNA construct will be co-delivered by nucleofection to patient-derived iPSCs that are heterozygous for the G2019S mutation (generated under CIRM grant TR1-01246). The donor construct contains 1 kb of wild type (wt) LRKK2 genomic sequence (500 bps in each direction of the mutation). In a subpopulation of cells that contain ZFN-mediated DSB, HDR uses the donor as a template to repair the DSB as well as the mutation; the majority of the cells use NHEJ to resolve the DSB. Transfected (GFP-positive) cells are enriched through fluorescence-based cell sorting and replated on MEF feeder layers for single-cell cloning. Genomic DNA can be isolated from 200-250 clones, the region of interest amplified by PCR and subjected to digest by restriction enzymes SfcI and BsrDI. SfcI only cleaves unmodified G2019S allele; while BsrDI site is destroyed if deletion or insertion has occurred at the site of DSB (suggesting NHEJ). Single cell-derived clones that contain 2 wt alleles (gene correction) will lose the SfcI site and retain BsrDI site on both alleles, while clones that contain intact wt allele and disrupted G2019S allele will retain BsrDI on one allele. Clones meet these criteria will be subject to sequencing analysis to confirm the presence of 2 wt LRRK2 alleles for G2019S corrected cells, and to identify those have frameshift mutations on the mutant allele and unmodified wt allele. Before further functional characterization of gene-corrected or G2019S disrupted iPSC clones, cytogenetic analysis will be performed to confirm they have normal karyotype, and their pluripotent state will be verified by expression of the pluripotency markers (OCT4, NANOG and SOX2), as well as ability to form all three developmental germ layers in teratoma-formation assays.

Alternatively, LRRK2 gene modification can be performed in patient-derived fibroblasts and iPSCs derived from ZFN/donor-transfected fibroblasts pool. This approach provides an alternative path to corrected iPS cells, and because fibroblasts are easier to maintain in cell culture, they can be transfected with significantly higher efficiency (>90% using nucleofection). Patient-derived fibroblasts are then nucleofected with LRRK2 ZFN expression vectors and the donor construct, cel-1 nuclease assay will be performed on a sub-population of transfected cells to confirm that efficient cleavage by ZFNs has occurred at the LRRK2 locus. The transfected pool is used for iPSC derivation; the resultant iPSC clones subjected to genotype analysis. Clones with 2 wt LRRK2 alleles, as well as those with frameshift mutation on the G2019S allele and intact wt allele, will be identified and their pluripotency verified before additional functional characterization.

Example 24

De Novo Creation of LRRK2 G2019S Mutation in Normal iPS Cells

LRRK2 ZFNs can also be used to introduce DSBs to the LRRK2 locus in iPSCs derived from normal subjects, and HDR can be invoked for de novo creation of monoallelic G2019S mutation; the resultant iPS cell lines can provide powerful evidence whether the G2019S mutation is sufficient for producing PD-related phenotypes in terms of increased kinase activity and ultimately pathological manifestation of PD in dopaminergic neurons derived from iPS cells.

For these experiments, iPS cells from normal subjects are used, and the donor construct contains the nucleotide that introduces the G2019S mutation. The desired clone will contain SfcI site on one allele and BsrDI on both alleles, clones with the expected digest pattern will be sequenced to verify the engineered mutation. Alternatively, a non-integrating lentiviral vector is used deliver both the ZFNs and the donor to patient-derived iPSCs.

Example 25

Assessment of LRRK2 Protein and Kinase Activity in ZFN-Modified Cell Lines

The first functional measures to assess the impact of the ZFN-mediated gene editing are the direct effect on the LRRK2 protein and LRRK2 kinase activity in iPS cells. Immunoblot analysis is used to ensure the ZFN-editing does not affect the steady state accumulation of LRRK2 when compared to wild type cells. The amount of LRRK2 kinase activity in edited iPS cells is determined using the ability to immunoprecipitate and assay endogenous LRRK2 against a novel and specific peptide sequence-Nictide15. The amount of LRRK2 kinase activity is evaluated in these cells by immunoprecipitation of endogenous LRRK2 from wild-type, G2019S het and ZFN mediated wild-type reversions, followed by assaying the activity against Nictide in immune complex kinase assays. Another assay of LRRK2 kinase activity is based on the demonstration that LRRK2 kinase activity potentiates a feedback phosphorylation event on Serines 910 and 935. Monitoring these sites can detect the loss of LRRK2 kinase activity. LRRK2 kinase activity is monitored using phospho-specific antibodies against phosphoserine 910 and phosphoserine 93516. Other antibodies targeted to LRRK2 constitutive phosphorylation sites as well as against autophosphorylation sites may also serve as useful readouts of LRRK2 kinase activity. Having isogenic control cell lines adds great precision to these experiments. Alternatively, in situ or immunofluorescence techniques of the disclosure can be used, e.g., examination of phosphoserine 910/935 phosphorylation by immunohistochemical approaches.

Example 26

Evaluation of a PD-Related Phenotype in ZFN-Modified Cell Lines in Differentiated Midbrain Dopaminergic Neurons mDA neurons have been derived that show characteristics of A9 mDA neurons of the substantia nigra. The expression (RT-PCR and IHC) of other midbrainconsistent markers can be measured in these mDA neurons. Neuronally differentiated iPS cells can be examined for signs of spontaneous pathology starting with simple measures of mDA cell abundance (% DA neurons after differentiation) and general morphological attributes such as inclusion bodies, or dystrophic neuritis and functional dopamine release measured by HPLC).

Stress responses can be compared in mDA neurons from the generated panel of 'repaired', disrupted, and created G2019S mutation and unmodified 'original' iPS lines. Several clones from the same lines can be tested as well as lines from unrelated LRRK2 carriers. Parameters to be examined include molecular signs of pathology of PD, which include biochemical markers of oxidative stress, a-synuclein overexpression, and mitochondrial and lysosomal dysfunction. Assays for disease-associated mechansisms include apoptosis (TUNEL, caspase activation), necrosis (CytoTox-Glo), 3) oxidative stress (glutathione, ROS and 4-EINE), 4) mitochondrial dysfunction (ATP-lite: ATP production, membrane potential, mitochondrial content). Protein aggregation of a-synuclein can be assessed with antibodies against total, phosphorylated and nitrated a-synuclein to detect aggregates, inclusion bodies, and neuritic pathology.

Neurons can be sampled for candidate gene profiling at multiple time points during the dopaminergic differentiation using a carefully selected set of neuronal markers as well as markers of specific pathology related to neurodegeneration of PD (oxidative stress genes, mitochondrial genes, lysosomal genes, axon-guidance pathway genes). Alternatively, global comparisons can be made for expression differences in these cell lines using commercially available microarray platforms for mRNAs to identify potential downstream targets or microRNAs, since there is recent evidence that LRRK2 regulates miRNA-mediated translational repression. The availability of isogenic controls avoids many confounding factors in data interpretation.

To further sensitize the disease model of this approach, disease LRRK2 cells and corrected cells can be subjected to known toxicants and stressors to see if they exhibit different responses. Possible agents for this approach include neurotoxicants such as MPTP/MPP+ (a neurotoxicant specific for dopaminergic neurons), 6-hydroxydopamine which induces cell death and oxidative stress, and the pesticide rotenone, a mitochondrial toxin.

Example 27

Disruption of Phosphorylation of LRRK2 Serines 955 and 973 by Parkinson's Disease Mutations and LRRK2 Inhibition I. Methods
A. Reagents and General Methods.

Tissue-culture reagents were from Life Technologies. The Flp-in T-REx system was from Invitrogen and stable cell lines were generated as per manufacturer instructions by selection with hygromycin. Restriction enzyme digests, DNA ligations and other recombinant DNA procedures were performed using standard protocols. DNA constructs used for transfection were purified from *Escherichia coli* DH5alpha using Qiagen plasmid Maxi kits according to the manufacturer's protocol. All DNA constructs were kindly provided by Dr. Dario Alessi (MRC-PPU, Dundee University, Dundee Scotland) except pcDNA5/FRT/TO +GFP-LRRK2-S860A, pcDNA5/FRT/TO +GFP-LRRK2-S955A, pcDNA5/FRT/TO +GFP-LRRK2-S973A, pcDNA5/FRT/TO +GFP-LRRK2-S976A, and pcDNA5/FRT/TO +GFP-LRRK2-S973A/S976A which were sub-cloned from the corresponding pCMV5-FLAG constructs.

B. Buffers.

Lysis Buffer contained 50 mM Tris/HCl, pH 7.4, 1 mM EGTA, 1 mM EDTA, 1 mM sodium orthovanadate, 10 mM sodium β-glycerophosphate, 50 mM NaF, 5 mM sodium pyrophosphate, 0.27 M sucrose, 1 mM Benzamidine and 1 mM phenylmethanesulphonylfluoride (PMSF) and was supplemented with 1% Triton X-100. Buffer A contained 50 mM Tris/HCl, pH 7.4, 50 mM NaCl, 0.1 mM EGTA and 0.27 M sucrose. Cell culture, treatments and cell lysis. HEK-293 cells were cultured in Dulbecco's Modified Eagle's medium supplemented with 10% FBS, 2 mM glutamine and 1×antimycotic/antibiotic solution. HEK-293 T-REx cell lines were cultured in DMEM supplemented with 10% FBS and 2 mM glutamine, 1X antimycotic/antibiotic, and 15 μg/ml Blasticidin and 100 μg/ml hygromycin. Cell transfections were performed by the polyethylenimine method. T-Rex cultures were induced to express the indicated protein by inclusion of 1 μg/ml doxycycline in the culture medium for 24 hours. Per 15 cm dish, cells were washed once with PBS and lysed in situ with 1.0 ml of lysis buffer on ice, then centrifuged at 15,000×g at 4° C. for 15 minutes. Protein concentrations were determined using the Bradford method with BSA as the standard.

C. Antibodies

Figure 14:
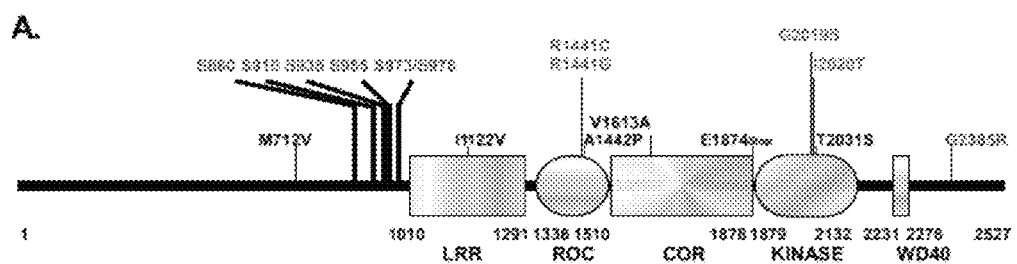
FIG. 14 shows a linear domain map of LRRK2 Amino acid boundaries of the domains are indicated above domain names (LRR, leucine Rich Repeat; ROC, Ras of Complex; COR, c-terminal of ROC; Kinase and WD40). Pathogenic mutations, non pathogenic mutations, and constitutive phosphorylation sites are indicated.

Antibodies against LRRK2 phosphosites were produced by Yenzyme Inc. Phosphoserine 910 antibodies were generated by injection of the keyhole limpet hemocyanin (KLH) conjugated phosphopeptide CLVKKKSNpSISVGE (SEQ ID NO: 1) (where pS is phosphoserine, Cys added for conjugation) into rabbits and was affinity purified by positive and negative selection against the phospho and de-phospho peptides respectively. Antibodies against LRRK2 phosphoserine 935 were generated by injection of the KLH conjugated phosphopeptide CLQRHSNpSLGPIFDH (SEQ ID NO: 2) (where pS is phosphoserine) into rabbit and was affinity purified by positive and negative selection against the phospho and de-phospho peptides respectively. Antibodies against LRRK2 phosphoserine 955 were generated by injection of the KLH conjugated phosphopeptide CRKRKILSpSDDSLR (SEQ ID NO: 3) into rabbit and were affinity purified by positive and negative selection against the phospho and de-phospho peptides respectively. Antibodies against LRRK2 phosphoserine 973/phosphoserine 976 were generated by injection of the KLH conjugated phosphopeptide CHMRHSDpSISpSSLA-SERE (SEQ ID NO: 4) into rabbits and were affinity purified by positive and negative selection against the phospho and de-phosphopeptides respectively. The LRRK2 phosphoserine 973/phosphoserine 976 antibody only recognizes the pS973 phosphosite as is shown in FIG. 14. Recombinant LRRK2 100-500 was generated by expression as a GST fusion protein in bacteria and purification on glutathione sepharose (obtained from Amersham) followed by cleavage of the GST moiety with Prescission Protease. Antibodies against total LRRK2 were generated by injection of LRRK2 100-500 into rabbits followed by affinity purification against uncleaved GST -100-500. Rabbit polyclonal antibodies against LRRK2 phosphothreonine 1491 were generated by the MJFF against a phospho Thr1491 peptide. Anti GFP monoclonal antibody was from Roche (clones 7.1 and 13.1, # 11814460001). The Nanotrap GFP-Trap A matrix was from ChromoTek (GTA-20). Anti-FLAG M2 antibody and affinity matrix were from Sigma (A2220). LiCOR Dyelight labelled 14-3-3 protein (recombinant, His tagged BMH1, a kind gift of Dr. Dario Alessi) was prepared as per the manufacturer's instructions and used to detect 14-3-3 binding. Anti-Hsp90 (heat-shock protein 90) antibody was from Cell Signalling Technology (#4877). Fluorescent secondary antibodies were from Li-COR (Lincoln NE) or Rockland immunochemicals (Rockland Ill.) LRRK2 Immunoprecipitation assays. Cell lysates were prepared in Lysis buffer (1.0 ml per 15 cm dish) and subjected to immunoprecipitation with GFP-trapA beads at 10 ul beads per 1.0 ml lysate for 1 hr. Beads were washed twice with Lysis Buffer supplemented with 300 mM NaCl, the twice with Buffer A. Immune complexes were boiled in Laemelli sample buffer and incubated at 70 degrees C. for 10 minutes. Immunoprecipitation Kinase Assay conditions. Wild-type LRRK2 was transiently expressed in HEK293 cells using polyethylenimine for approximately 36 hours, then cells were treated with DMSO or 1 μM LRRK2-IN1 for 90 minutes. Lysates were then subjected to immunoprecipitation with anti-FLAG M2 agarose at a ratio of 1 μl beads per 100μg of lysate for 2 hours. Immune complexes were washed three times with lysis buffer supplemented with 300 mM NaCl, followed by three washes with buffer A. Immune complexes were subjected to in vitro kinase assay by incubation with 50 mM Tris [pH 7.4], 0.1 mM EGTA, with or without 100 μM ATP and in the presence or absence of LRRK2-IN1. Reaction products were analyzed by immunoblot analysis.

D. Fluorescence Microscopy.

HEK-293 Flp-in T-REx cells harbouring GFP tagged LRRK2 and PD associated mutations were plated in 4-well glass bottom, CC2 coated chamber slides (Nunc). One day after plating, cells were induced with 1 μg/ml doxycycline and 24 hr later, cells were fixed in 4% paraformaldehyde buffered in phosphate buffered saline (purchased from Electron Microscopy Sciences, #15710). Cells were imaged under on a Nikon TiE microscope with a 60X objective.

II. Results

FIG. 14 depicts phopshorylation of LRRK2. LRRK2 is phosphorylated on Serines 955 and 973. Mass spectrometry reports describe phosphorylation sites on LRRK2 in a cluster of serines in the amino terminus, preceding the LRR domain. Phosphorylation of LRRK2 on Serines 910 and 935 in this cluster of constitutive phosphorylation sites mediates an interaction with 14-3-3 proteins and is essential for maintaining a diffuse cytoplasmic localization. In order to further characterize this cluster of phosphorylation sites, HEK293 T-REx Flp-in cell lines were generated that express GFP tagged, full length LRRK2 and the indicated mutants in a stable and inducible manner These lines include a GFP control, kinase inactive LRRK2 [D2017A], phospho site mutations [Ser910A Ser935A, Ser955A, Ser973A Ser976A and combinations thereof], inhibitor resistant mutants [A2016T and A2016T+G2019S], non pathogenic PD associated mutations [M712V, I1122V, A1442P, V1613A, E1874Stop and T2031S], pathogenic PD mutants [R1441G/C, G2019S and I2020T], and the susceptibility factor [G2385R].

Figure 15:
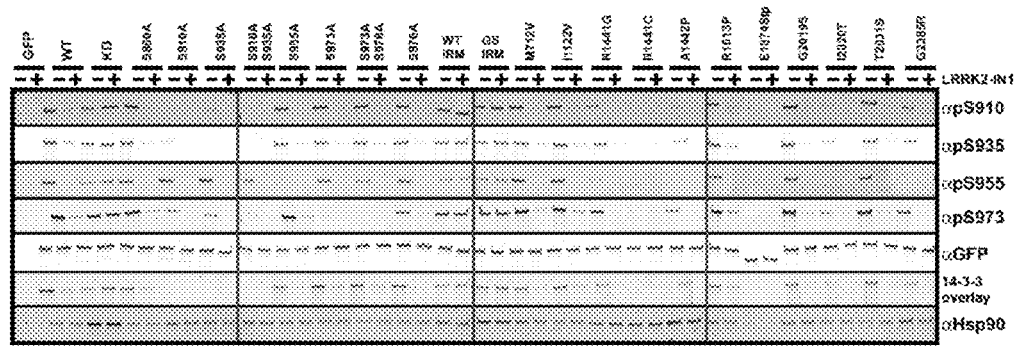
FIG. 15 shows analysis of LRRK2 pSer955 and pSer973 phosphorylation. The indicated variants of full-length GFP-tagged LRRK2 were expressed from a stable and inducible locus in HEK293 T-REx cells and subjected to immunoprecipitation analysis. Immunoprecipitates were subjected to immunoblot analysis with anti-GFP, and anti-phospho-Ser910 (αpS910), anti-phospho-Ser935 (αpS935), anti-phospho-Ser955 (αpS955), and anti-phospho-Ser973 (αpS973) antibodies. 14-3-3 binding to the LRRK2 variants was assessed by 14-3-3 far-western blot analyses. All blots were co-probed with phospho antibody and GFP (total protein) monoclonal antibody and analyzed by Odyssey® LI-COR analysis; a representative total GFP blot is shown. Hsp90 co-precipitation was assessed by αHsp90 immunoblotting. Data are representative of at least two experiments and were also seen with alternatively FLAG-tagged variants of LRRK2.

Cultures were treated with doxycycline and either treated with 1 µM LRRK2-IN1 or DMSO vehicle for 90 minutes. The TritonX-100 soluble fraction was subjected to GFP nano trap immunoaffinity chromatography; a representative aGFP immunoblot of these immunoprecipitates is shown (aGFP, FIG. 15). To specifically detect the amino terminal phosphosites, phosphoantibodies were generated against phosphoserine 910, phosphoserine 935, phosphoserine 955 and phosphoserine 973.

To ensure specificity, antibodies were tested against the corresponding Ser to Ala mutations of LRRK2. The antiphosphoserine 910 and 935 specifically recognize phosphorylated Ser910 and Ser935 (FIG. 15), not their Alanine mutations. The apSer955 and apSer973 antibodies efficiently recognize phosphorylated LRRK2 on Serines 955 and 973 and do not recognize Ser955Ala or Ser973Ala mutations, confirming that these sites are bone fide LRRK2 phosphorylation sites. Consistent with these results, a diphosphorylated peptide has been identified showing both Ser973 and Ser976 as phosphosites. The peptide used as an immunogen displayed both pSer973 and pSer976, however this antibody recognizes a Ser976Ala mutation as efficiently as it does wild-type LRRK2 indicating a specificity for pSer973. When mutations in Serines 910 and 935 are analyzed with these antibodies, no interdependence is observed with Ser955 phosphorylation on these important modifications. However, mutation of Serines 910 or 935 to Alanine results in a diminution of pSer973. LRRK2-IN1 treatment also resulted in reduced direct 14-3-3 association. FIG. 16 shows an alignment of Serines 860, 910, 935, 955 and 973; the primary amino acid sequence surrounding these sites reveals that Serines 910 935 and 973 bear striking similarity except for an Asp at the −1 position at Ser973, instead of an Asn at the −1 for Ser910 and Ser935. The apparent interdependence could reflect that the same or a similar kinase modifies these residues processively, however this remains to be tested. The direct association of 14-3-3 with LRRK2 was assessed by 14-3-3 overlay assay using fluorescent dye labeled recombinant 14-3-3.

Mutation of Serines 910 and 935 disrupted 14-3-3 binding and mutation of Ser955 and 973 had no effect on direct 14-3-3 binding. There was no difference in the amounts of Hsp90 co-immunoprecipitation among the phospho-mutants, however a consistent increase in Hsp90 association with kinase inactive LRRK2 was observed and no Hsp90 was retrieved in the E1874stop mutant. These data indicate that Hsp90 associates with the kinase domain of LRRK2, and is consistent with previous reports REF. Phosphorylation of Serines 955 and 973 is regulated by LRRK2 kinase activity.

We evaluated the phosphorylation status of 955 and 973 under a variety of conditions to characterize the phosphorylation of 955 and 973. The selective kinase inhibitor of LRRK2, LRRK2-IN1, potently inhibits LRRK2 in cell culture model systems and in vivo. Treatment of T-REx cells expressing active LRRK2 with LRRK2-IN1 results in a complete dephosphorylation of Serines 910/935, as well as the dephosphorylation of Serines 955 and 973. This LRRK2-IN1 induced dephosphorylation was observed in all mutants that had detectable levels of phosphorylation in the absence of inhibitor (−). Similar phosphorylation levels of 955 and 973 were observed in inhibitor resistant mutants [Ala2016Thr and Gly2019Ser+Ala2016Thr] regardless of LRRK2-IN1 treatment, demonstrating that the LRRK2-IN1 effect is due to specific inhibition of LRRK2 kinase activity. Just as treatment with H-1152 and Sunitinib did not perturb a basal level of LRRK2 phosphorylation at 910/935 in kinase inactive mutants, no change was observed in phosphorylation of Serines910 and 935 or in 955 and 973 after LRRK2-IN1 treatment of kinase inactive mutants. This low level of modification that is unperturbed by LRRK2-IN1 treatment could be a basal level of phosphorylation observed when cells are exposed to the expression of a non-natural kinase inactive mutant. Additionally, it was observed that the PD associated mutation E1874Stop, which lacks the LRRK2 kinase domain, is also not modified on Serines 955 or 973. The kinase domain, regardless of the presence of inactivating mutations, is therefore likely necessary for potentiation of feedback phosphorylation back to the amino terminal cluster. PD mutations disrupt phosphorylation of Serines 955 and 973. Pathogenic PD associated mutations that have an increased propensity to aggregate, LRRK2 [R1441C/G/H, Y1699C, I2020T], are not modified on serines 910 or 935, and therefore do not bind 14-3-3.

The impact of LRRK2 [R1441C/G, I2020T] as well as G2019S and other non-pathogenic PD associated mutations was assessed on the phosphorylation of Serines 955 and 973. Aggregation prone/non-14-3-3 binding mutations were not modified and did not show reduced modification on Serines 955 or 973, as has been observed for Serines 910 and 935. The risk factor mutation G2385R also induced reduced phosphorylation of Serines 910, 935, 955, and 973. Ser955 was more heavily impacted by G2385R than phosphorylation of Serines 910, 935 or 973.

Figure 17:
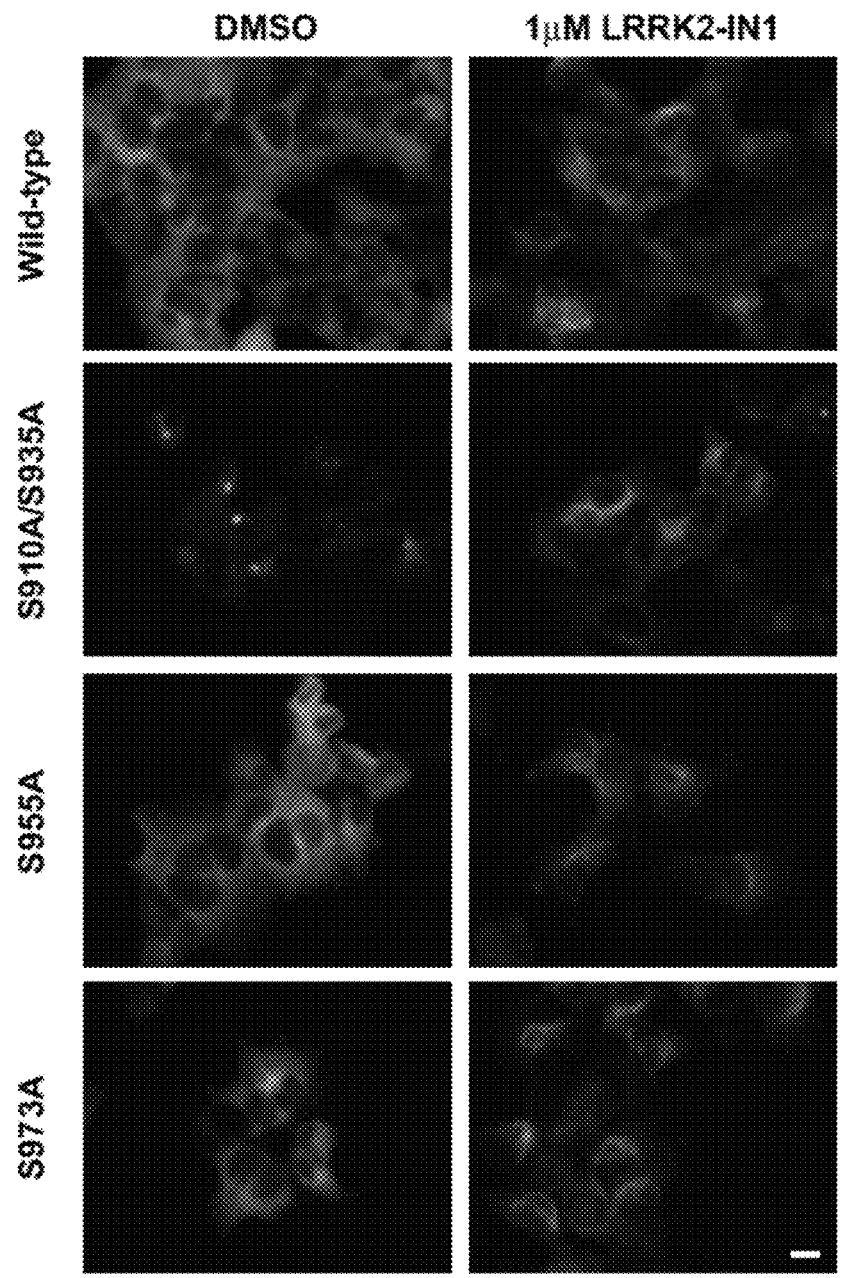
FIG. 17 shows Ser955Ala and Ser973Ala Localization. T-REx cells lines harboring the indicated LRRK2 variants were induced for 24 h with 1 µg/ml doxycycline to induce expression of GFP-LRRK2. After induction, cells were exposed to vehicle control (DMSO) or 1 µM LRRK2-IN1 for 90 minutes, then fixed with paraformaldehyde and GFP fluorescence was imaged. Representative fluorescent micrographs of cultures for the indicated phosphosite mutants in the presence and absence of inhibitor are shown, localization analysis was performed at least three times. White scale bar represents 10 microns.

FIG. 17 shows localization of Ser955Ala and Ser973Ala mutations. Mutation of Serines 910 and 935, individually or in combination, induces the accumulation of LRRK2 in the cytoplasm of HEK293 cells Inhibition of LRRK2 induced re-localization of the GFP tagged enzyme to intracellular puncta, large accumulations and microtubule like structures. Localization of Ser955Ala and Ser973Ala was comparable to wild-type LRRK2 localization and displayed no aggregation phenotype similar to 910/935. Treatment of cells expressing GFP-LRRK2 Ser910Ala/Ser935Ala, Ser955Ala, and Ser973Ala with LRRK2-IN1 resulted in a similar relocalization pattern compared to wild-type LRRK2 treated with LRRK2-IN1. These data indicate that cytoplasmic inclusions induced by loss of 14-3-3 binding due to Ser910Ala/Ser935Ala mutations are distinct from those induced by acute inhibition of LRRK2.

Figure 18:
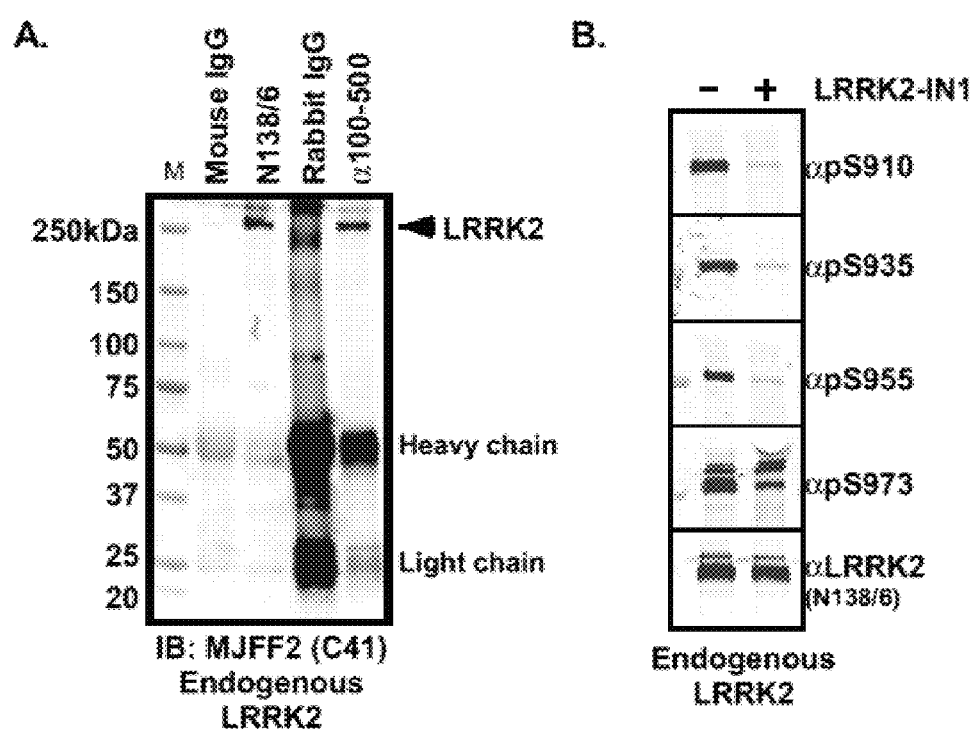
FIG. 18 shows data demonstrating that endogenous LRRK2 is phosphorylated on Ser955 and 973. A) Endogenous LRRK2 was immunoprecipitated from Swiss 3T3 cells with a mouse monoclonal anti LRRK2 clone N138/6 (NeuroMab) and rabbit polyclonal anti-LRRK2 (α100-500) antibody. Control immunoprecipitations are with species specific immunoglobulin (IgG). Immunoprecipitates were immunoblotted with MJFF2 (C41). Arrowhead indicates LRRK2 and antibody heavy and light chains are labeled. B) Endogenous LRRK2 was immunoprecipitated from Swiss 3T3 cells treated with DMSO control (−) or with LRRK2-IN1 (+) for 90 min Immunoprecipitates were subjected to immunoblot analysis with the indicated phospho antibodies. Blots were co-probed with phospho antibody as well as N138/6 monoclonal antibody and analyzed by Odyssey® LI-COR analysis; a representative total blot is shown.

FIG. 18 shows phosphorylation of endogenous LRRK2. Isolation and analysis of endogenous LRRK2 is an essential component of elucidating the in vivo roles of the enzyme. The first reported antibody capable of immunoprecipitating LRRK2 was produced in sheep against an antigen comprising amino acids 100-500 of the human enzyme. We have developed analogous antibodies in rabbits that immunoprecipitate LRRK2. FIG. 18A shows the ability of this reagent to isolate LRRK2 from Swiss3T3 cells. Additionally, we have characterized a mouse monoclonal antibody (NeuroMab) that is also capable of immunoprecipitating endogenous LRRK2. In order to determine if Ser955 and Ser973 are phosphorylated on endogenous protein, these antibodies were used in combination to immunoprecipitate endogenous LRRK2 from lysates of Swiss3T3 cells treated with LRRK2-IN1 or vehicle control. Immunoblotting the immunoprecipitates with the apSer910, apSer935, apSer955 and apSer973 antibodies reveals that endogenous LRRK2 is phosphorylated on Serines 955 and 973, similar to Ser910 and Ser935.

Figure 19:
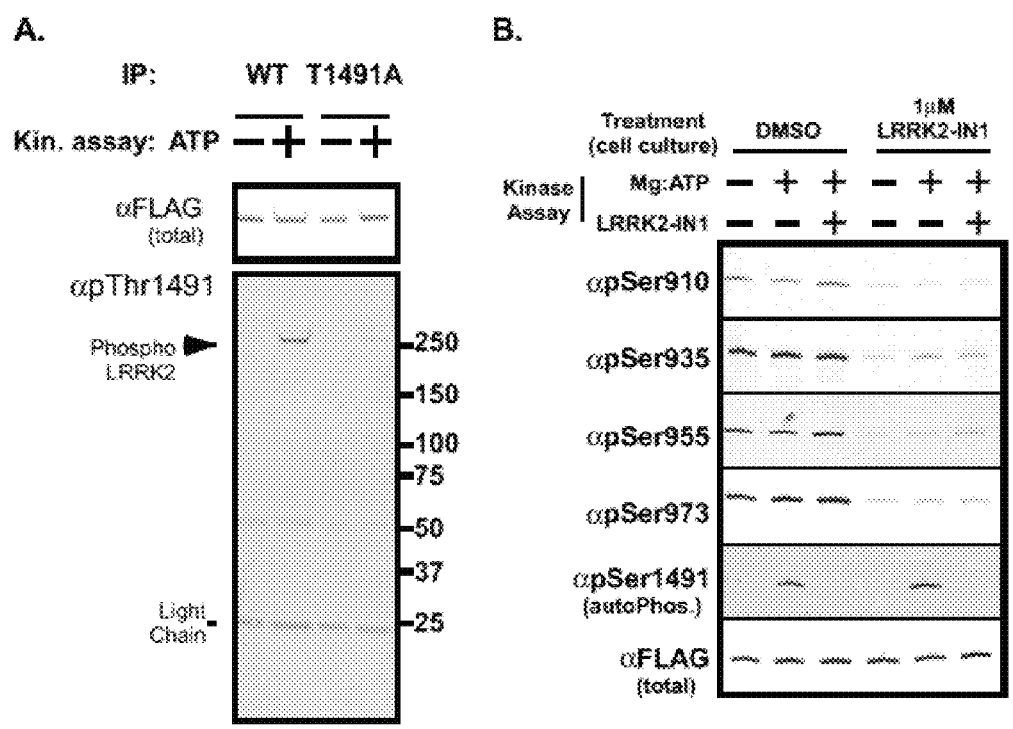
FIG. 19 shows data demonstrating that LRRK2 does not re-phosphorylate Ser955 and 973 in vitro after in vivo dephosphorylation. A) Transiently expressed, FLAG-tagged wild-type or Thr1491Ala (T1491A) LRRK2 was subjected to immunoprecipitation-kinase assay, using anti-FLAG M2 agarose, in the presence (+) or absence (−) of ATP. Reaction products were probed with antiphospho-Ser1491 (αpThr1491) antibodies in the presence of dephosphopeptide. Blots were reprobed with anti-FLAG (αFLAG) for total protein control. B) Transiently expressed wild-type LRRK2 was immunoprecipitated from HEK293 cells treated with DMSO or LRRK2-IN1 to induce dephosphorylation of the constitutive sites (Treatment cell culture). Immunoprecipitates were extensively washed then subjected to in vitro kinase assay in the presence or absence of ATP, in the presence or absence of LRRK2-IN1. Reaction products were immunoblotted with antiphospho-Ser1491 (αpThr1491), anti-phospho-Ser910 (αpS910), anti-phospho-Ser935 (αpS935), anti-phospho-Ser955 (αpS955), and anti-phospho-Ser973 (αpS973) antibodies.
Figure 20:
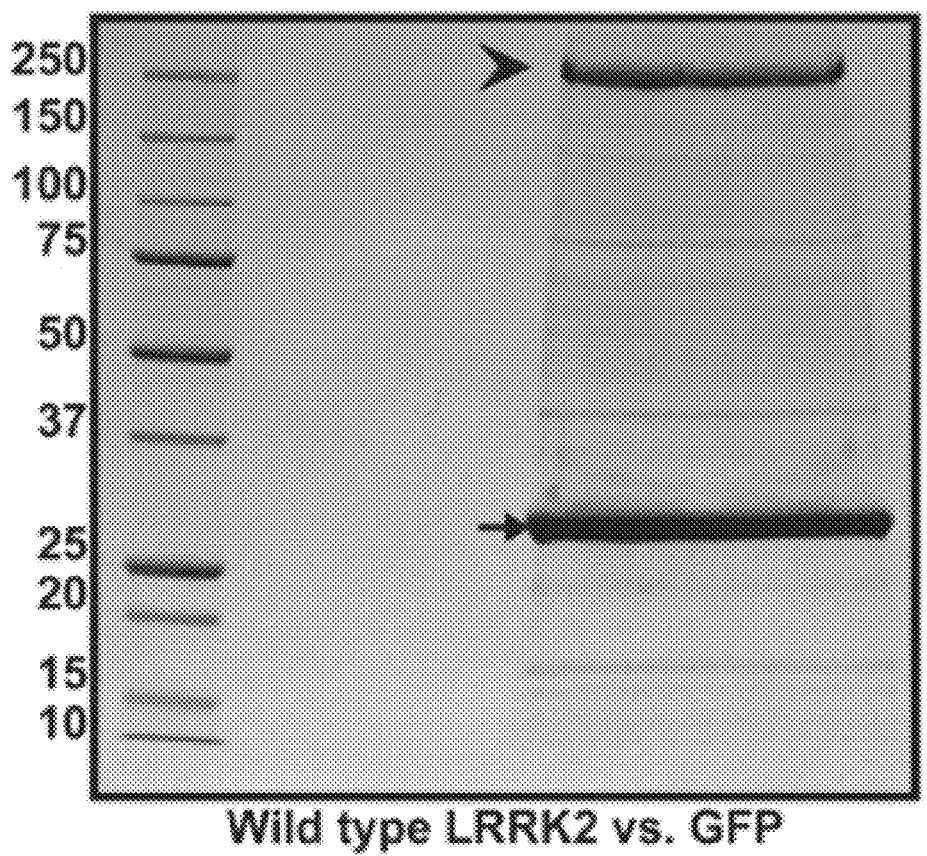
FIG. 20 shows a gel from which quantitative mass spectrometry (MS) 14-3-3 was identified as an LRRK2 interactor. HEK-293 cells stably expressing GFP, wild-type full-length GFP-LRRK2 or full-length GFP-LRRK2(G2019S) mutant were cultured for multiple passages in either R6K4 SILAC medium (GFP-LRRK2) or R10K8 SILAC medium [GFP-LRRK2(G2019S)] or normal ROKO SILAC medium (GFP). Cells were lysed and equal amounts of lysates from GFP and GFP-LRRK2 were mixed. Migration of the LRRK2 band is indicated with an arrowhead and the GFP band is indicated with an arrow. Molecular-mass markers (kDa) are indicated on the left-hand side of the gels. The entire lane from each gel was excised, digested with trypsin and processed for MS. Each sample was analysed with Orbitrap MS and quantified using MaxQuant (version 13.13.10).

FIG. 19 shows Characterization of anti-Thr1491 autophosphorylation antibody. In collaboration with the Michael J Fox Foundation's Antibodies Working Group, a rabbit polyclonal antibody against phosphorylated Ser1491 was developed. Ser1491 is known to be a site of LRRK2 autophosphorylation. Wild-type and Ser1491Ala variants of LRRK2 were transiently expressed in HEK293 cells and following immunoprecipitation-kinase assay, immunoprecipitates were probed with anti-phospho-Thr1491 (pThr1491) antibody. The anti-pThr1491 antibody does not recognize a Thr1491Ala mutant, and only reacts with LRRK2 incubated in the presence of magnesium:ATP Minimal reactivity against pThr1491 in wild-type LRRK2 expressed in cells may indicate this site is modified to a low stoichiometry in vivo and that immunological detection is only capable after in vitro autophosphorylation.

LRRK2 does not phosphorylate Serines 955 and 973. The proposed feedback phosphorylation mechanism that leads to the modification of Serines 910 and 935 appears to apply to LRRK2 Ser955 and Ser973. Active LRRK2 that was dephosphorylated at these sites was generated and it was determined if in vitro autophosphorylation could rephosphorylate these sites. HEK 293 cells transiently expressing FLAG tagged wild-type LRRK2 were treated with LRRK2-IN1 to dephosphorylate LRRK2, or DMSO vehicle control. LRRK2 was immunoprecipitated with anti-FLAG agarose and immunoprecipitates were washed to remove compound. Washed immunoprecipitates were subjected to in vitro autophosphorylation kinase assay by incubation in the presence or absence of magnesium:ATP, with or without LRRK2-IN1. The LRRK2 enzyme purified was able to autophosphorylate as revealed by immunoblotting with anti-pThr1491 antibody. Immunoblotting with anti-pSer910, anti-pSer935, anti-pSer955 and anti-pSer973 antibodies revealed that LRRK2 was indeed dephosphorylated at the corresponding residues and, importantly, that the phosphorylation of these sites does not increase in conditions that are permissive for autophosphorylation (see anti-pThr1491 analysis). These data strongly argue that LRRK2 does not autophosphorylate on Serines 910, 935, 955 and 973. Cumulatively, the data indicate that LRRK2 Serines 955 and 973 are regulated similarly to Serines 910 and 935. The downstream kinase(s) and phosphatases responsible for the regulation of this constitutive phosphorylation cluster have yet to be identified but are now targets for pathway development around LRRK2 activities.

Example 28

Disruption of LRRK2 Interactions and Localization by Multiple Parkinson's Disease-Associated Mutations I. Methods A. Reagents and General Methods Tissue-culture reagents were from Life Technologies. P81 phosphocellulose paper was from Whatman and [γ-32P] ATP was from PerkinElmer. All peptides were synthesized by Pepceuticals. The Flp-in T-REx system was from Invitrogen, and stable cell lines, generated according to the manufacturer's instructions by selection with hygromycin. Restriction enzyme digests, DNA ligations and other recombinant DNA procedures were performed using standard protocols. All mutagenesis was carried out using the QuikChange® site-directed mutagenesis kit (Stratagene). DNA constructs used for transfection were purified from *Escherichia coli* DH5α cells using Qiagen or Invitrogen plasmid Maxi kits according to the manufacturer's instructions. All DNA constructs were verified by DNA sequencing, which was performed by the Sequencing Service, School of Life Sciences, University of Dundee, Dundee, Scotland, U.K., using DYEnamic ET terminator chemistry (Amersham Biosciences) with automated DNA sequencers (Applied Biosystems).

B. Buffers

Lysis buffer contained 50 mM Tris/HCl, pH 7.5, 1 mM EGTA, 1 mM EDTA, 1% (w/v) (1 mM) sodium orthovanadate, 10 mM sodium β-glycerophosphate, 50 mM NaF, 5 mM sodium pyrophosphate, 0.27 M sucrose, 1 mM benzamidine and 2 mM PMSF and was supplemented with 1% Triton X-100. Buffer A contained 50 mM Tris/HCl, pH 7.5, 50 mM NaCl, 0.1 mM EGTA and 0.27 M sucrose. k phosphatase reactions were carried out in buffer A supplemented with 1 mM MnCl2, 2 mM DTT (dithiothreitol) and 0.5 μg of λ phosphatase. MARK3 (microtubule affinity-regulating kinase 3) was from Upstate Biotechnology (#05-680).

C. Cell Culture, Treatments and Cell Lysis

HEK-293 (human embryonic kidney) and Swiss 3T3 cells were cultured in DMEM (Dulbecco's modified Eagle's medium) supplemented with 10% FBS (fetal bovine serum), 2 mM glutamine and 1×antimycotic/antibiotic solution (1×penicillin/streptomycin/amphotericin B; Invitrogen). HEK-293 T-Rex REx cell lines were cultured in DMEM supplemented with 10% FBS and 2 mM glutamine, 1×antimycotic/antibiotic solution, 15 μg/ml blastocidin and 100 μg/ml hygromycin. Cell transfections were performed by the polyethyleneimine method. T-REx cultures were induced to express the indicated protein by inclusion of 1 μg/ml doxycycline in the culture medium for 24 h. Per 15 cm dish, cells washed once with PBS and lysed insitu with 1.0 ml of lysis buffer, on ice, then centrifuged at 16 000 g at 4° C. for 10 min Protein concentrations were determined using the Bradford method with BSA as the standard.

D. SILAC (Stable Isotope Labelling of Amino Acids)

SILAC DMEM (high glucose without NaHCO3, L-glutamine, arginine, lysine and methionine; Biosera #A0347) was prepared with 10% dialysed FBS (Hyclone) and supplemented with methionine, glutamine, NaHCO$_3$ and labelled or unlabelled arginine and lysine. Cells harbouring GFP-tagged proteins were cultured in SILAC DMEM for three passages at a 1:10 ratio with the following isotopic labelling. For GFP compared with wild-type LRRK2, L-arginine (84 μg/ml; Sigma-Aldrich) and L-lysine (146 μg/ml; Sigma-Aldrich) were added to the GFP 'light' medium, whereas 13C-labelled L-arginine and 13 C-labelled L-lysine (Cambridge Isotope Laboratory) were added to the GFP-LRRK2 wild-type 'heavy' medium at the same concentrations. For the GFP compared with LRRK2(G2019S) experiments, Larginineand L-lysine were added to the GFP 'light' medium and 13C/15N-labelled L-arginine and 13C/15N-labelled L-lysine (Cambridge Isotope Laboratory) to the GFP-LRRK2(G2019S) 'heavy' medium. The amino acid concentrations are based on the formula for normal DMEM (Invitrogen). Once prepared, the SILAC medium was mixed well and filtered through a 0.22-μm filter (Millipore). Metabolically labelled cells were induced to express GFP or the GFP-LRRK2 fusion protein for 24 h by inclusion of doxycycline in the culture medium.

E. SILAC Labelling and MS

Cells metabolically labelled and induced to express GFP, wildtype LRRK2 or LRRK2(G2019S) were lysed in lysis buffer supplemented with 1% Triton X-100 at 0.5 ml per 10 cm dish. For each condition individually, 9 mg of cell lysate was subjected to individual immunoprecipitation with a 20 μl of bed volume of GFP-binder agarose beads for 1 h at 4° C. Beads were washed once with 5 ml and then with 10 ml of lysis buffer supplemented with 1% Triton-X 100 and 300 mM NaCl. Beads were then washed once with 5 ml and then once with 10 ml of storage buffer. Bead-associated proteins were eluted with 1×NuPAGE LDS sample buffer (Invitrogen) for 10 min at 70° C. then passed through a 0.22 µm Spin-X column (Corning). Control GFP eluates were combined with either eluates of wild-type LRRK2 or LRRK2(G2019S) in equal amounts and reduced and alkylated as above. Samples were resolved on a 12% Novex gel for only one half of the gel. Gels were stained with Colloidal Blue overnight and destained for 3 h. The entire lane was excised in nine bands in total and digested with trypsin. The digests were separated on a Biosphere C18 trap column [0.1 mm (internal diameter)×2 mm; Nanoseparations] connected to a PepMap C18nano column (75 µm×15 cm; Dionex Corporation) fitted to a Proxeon Easy-LC nanoflow LC-system (Proxeon Biosystems) with solvent A (2% acetonitrile/0.1% formic acid/98% water) and solvent B (90% acetonitrile/10% water/0.09% formic acid). Samples (10 µl; a total of 2 µg of protein) were loaded with a constant flow of 7 µl/min on to the trap column in solvent A and washed for 3 min at the same flow rate. After trap enrichment, peptides were eluted with a linear gradient of 5-50% solvent B over 90 min with a constant flow of 300 nl/min The HPLC system was coupled to a linear ion-trap—orbitrap hybrid mass spectrometer (LTQ-Orbitrap XL, Thermo Fisher Scientific) via a nanoelectrospray ion source (Proxeon Biosystems) fitted with a 5 cm Picotip FS360-20-10 emitter. The spray voltage was set to 1.2 kV and the temperature of the heated capillary was set to 200° C. Full-scan MS survey spectra (m/z 350-1800) in profile mode were acquired with the LTQ-Orbitrap with a resolution of 60 000 after accumulation of 500 000 ions. The five most intense peptide ions from the preview scan in the LTQ-Orbitrap were fragmented by collision-induced dissociation (normalized collision energy 35%, activation Q 0.250 and activation time 30 ms) in the LTQ-Orbitrap after the accumulation of 10 000 ions. Maximal filling times were 1000 ms for the full scans and 150 ms for the MS/MS scans. Precursor ion charge state screening was enabled and all unassigned charge states, as well as singly charged species, were rejected. The lock mass option was enabled for survey scans to improve mass accuracy. Data were acquired using the Xcalibur software.

F. LC-MS Data Analysis using MaxQuant

The raw mass spectrometric data files obtained for each experiment were collated into a single quantified dataset using MaxQuant (version 1.0.13.13) and the Mascot search engine (Matrix Science, version 2.2.2) software. Enzyme specificity was set to that of trypsin. Other parameters used within the software: variable modifications, methionine oxidation; database, target-decoy human MaxQuant (ipi.HUMAN.v3.52.decoy) (containing 148,380 database entries); labels, R6K4 (for GFP compared with wild-type LRRK2) or R10K8 [for GFP compared with LRRK2 (G2019S)]; MS/MS tolerance, 0.5 Da; top MS/MS peaks per 100 Da, 5; maximum missed cleavages, 2; maximum of labelled amino acids, 3; FDR (false discovery rate), 1%.

G. Phosphorylation Site Identification by MS

Endogenous and recombinant LRRK2 was immunoprecipitated from 50 mg of Swiss 3T3 lysate or T-REx cells induced to express FLAG-LRRK2 cell lysate using anti-LRRK2-(100-500)- or anti-FLAG-agarose respectively. Immunoprecipitates were eluted from the affinity matrices using 2× LDS sample buffer or 200 µg/ml FLAG peptide then filtered through a 0.2 µm Spin-X column before reduction with 10 mM DTT and alkylation with 50 mM iodoacetamide. Samples were heated for 10 min at 70° C. and resolved on 4-12% Novex gels before staining with Colloidal Blue (Invitrogen). Bands corresponding to LRRK2 were excised and digested with trypsin as described previously. Samples were analysed on an LTQ-Orbitrap XL mass spectrometer as described above, except that the top five ions were fragmented in the linear ion-trap using multistage activation of the neutral loss of phosphoric acid from the parent ion (neutral loss masses=49,32.33 and 24.5 for z =2, 3 and 4 respectively). Mascot generic files were created from the raw files using raw2msm (a gift from Professor Matthias Mann, Max Planck Institute of Biochemistry, Martinsried, Germany) and were searched on a local Mascot server using the IPI (International Protein Index) mouse database for endogenous LRRK2 or the IPI human database for recombinant LRRK2.

H. Immunological Procedures

Cell lysates (10-30 µg) were resolved by electrophoresis on SDS/polyacrylamide gels or Novex 4-12% gradient gels, and electroblotted on to nitrocellulose membranes. Membranes were blocked with 5% (w/v) skimmed milk in TBST [Tris-buffered saline with Tween 20: 50 mM Tris/HCl, pH 7.5, 0.15 M NaCl and 0.1% (v/v) Tween 20]. For phospho-specific antibodies, primary antibody was used at a concentration of 1 µg/ml, diluted in 5% skimmed milk in TBST with the inclusion of 10 µg/ml dephosphorylated peptide. All other antibodies were used at 1 µg/ml in 5% (w/v) milk in TBST. Detection of immuno-complexes was performed using either fluorophoreconjugated secondary antibodies (Molecular Probes) followed by visualization using an Odyssey infrared imaging system (LI-COR Biosciences) or by horseradish-peroxidase-conjugated secondary antibodies (Pierce) and an enhanced chemiluminescence reagent. For immunoprecipitations, antibody was non-covalently coupled to Protein G-Sepharose at a ratio of 1 µg of antibody/µl of beads, or anti-FLAG M2-agarose was utilized. Cell lysates were incubated with coupled antibody for 1 h. To assess Ser935 phosphorylation, total LRRK2 levels and 14-3-3 binding in mouse tissues, LRRK2 was immunoprecipitated from 6 mg of wholetissue lysate using 15 µg of antibody coupled to 15 µl of Protein G-Sepharose. Ser910 phosphorylation was assessed following immunoprecipitation from 10 mg of tissue lysate. Immunocomplexes were washed twice with lysis buffer supplemented with 0.3 M NaCl and twice with buffer A. Precipitates were re-suspended in LDS sample buffer and subjected to immunoblot analysis. DIG (digoxigenin)-labelled 14-3-3 for use in overlay far-Western blot analysis. To directly assess 14-3-3 interaction with LRRK2, immunoprecipitates were electroblotted on to nitrocellulose membranes and blocked with 5% skimmed milk for 30 min After washing with TBST, membranes were incubated with DIG-labelled 14-3-3 diluted to 1 µg/ml in 5% BSA in TBST overnight at 4° C. DIG-labelled 14-3-3 was detected with horseradishperoxidase-labelled anti-DIG Fab fragments (Roche).

I. LRRK2 Immunoprecipitation Kinase Assays

Transfected cell lysates (500 µg) were subjected to immunoprecipitation with a 5 µbed volume of anti-FLAG-agarose for 1 h. Beads were washed twice with lysis buffer supplemented with 300 mM NaCl, and twice with buffer A. Peptide kinase assay were set up in a total volume of 50 µl with immunoprecipitated LRRK2 in 50 mM Tris/HCl, pH 7.5, 0.1 mM EGTA, 10 mM MgC12 and 0.1 mM [γ-32P]ATP (~300-500 c.p.m./pmol) in the presence of 200 µM long variant of the LRRKtide peptide substrate (RLGRDKYKTLR-QIRQGNTKQR (SEQ ID NO: 5)) or the Nictide peptide substrate (RLGWWRFYTLRRARQGNTKQR (SEQ ID NO: 6)). Reactions were terminated by applying 30 µl of the reaction mixture on to P81 phosphocellulose paper and immersing in 50 mM phosphoric acid. After extensive washing, the radioactivity in the reaction products was quantified by Cerenkov counting. One half of the remaining reaction was subjected to immunoblot analysis using the Odyssey infrared imaging system and specific activity is represented as c.p.m./independent density values. Affinity purification of 14-3-3 with a di-phosphorylated peptide encompassing Ser910 and Ser935 An N-terminally biotinylated di-phosphorylated peptide encompassing Ser910 and Ser935 (biotin-K KKSNpSISVGEFYRDAVLQRCSPNLQRHSNpSLGPIF (SEQ ID NO: 7)) was conjugated to streptavidin-agarose (1 μg peptide/μg of agarose). Aliquots of agarose beads (10 μl) were treated with or without λ phosphatase for 30 min at 30° C., with λ phosphatase being in the presence or absence of 50 mM EDTA. Conjugated beads were then incubated with 3 mg of HEK-293 cell lysate at 4° C. for 1 h. Following two washes with lysis buffer supplemented with 0.5 M NaCl, beads were boiled in LDS sample buffer and samples subjected to immunoblot analysis for 14-3-3.

Figure 21:
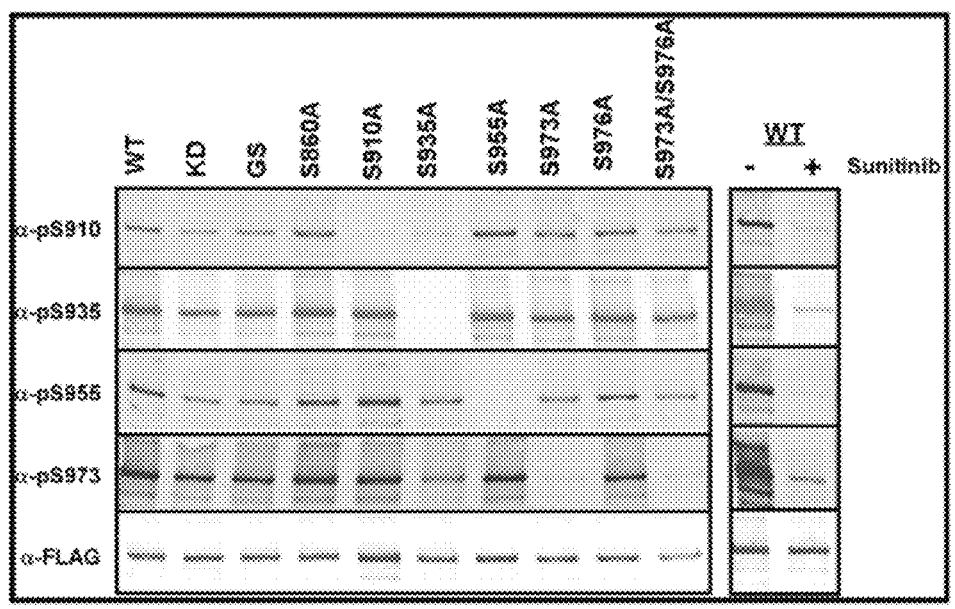
FIG. 21 shows phosphorylation of Serines 955 and 973 is dependent on LRRK2 kinase activity.

FIG. 21 shows that phosphorylation of Serines 955 and 973 is Dependent on LRRK2 Kinase Activity.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

---

What is claimed is:

1. An isolated phosphorylation site-specific antibody that specifically binds LRRK2 when the LRRK2 is phosphorylated at Ser955, wherein said antibody does not bind LRRK2 when not phosphorylated at said serine.

2. A method for detecting phosphorylation of LRRK2 in a subject, comprising the steps of
   a. obtaining a biological sample from said subject;
   b. contacting said biological sample with a phosphorylation site-specific antibody that specifically binds LRRK2 only when the LRRK2 is phosphorylated at Ser955; and
   c. detecting binding of said phosphorylation site-specific antibody to LRRK2.

3. The method of claim 2, wherein said subject is a human, dog, cow, horse, pig, sheep, goat, cat, mouse, rabbit, rat, or transgenic non-human animal.

4. The method of claim 2, wherein said subject is a cell.

5. The method of claim 4, wherein the cell is an induced pluripotent stem cell.

6. The method of claim 4, wherein the cell is a neuronal cell produced by differentiation of an induced pluripotent stem cell.

7. The method of claim 4, wherein the cell is a dopaminergic neuron cell produced by differentiation of an induced pluripotent stem cell.

8. The method of claim 5, wherein the induced pluripotent stem cell comprises a ZFN-edited genome.

9. The method of claim 2, wherein said detecting comprises proximity ligation assay.

10. The method of claim 2, further comprising correlating the results of said detecting with a functional assay.

11. The method of claim 10, wherein the functional assay is an assay for apoptosis, an assay for autophagy, or an assay for aggregation.

12. The method of claim 10, wherein the functional assay is an assay for interaction with a protein.

13. The method of claim 12, wherein the protein is 14-3-3.

14. The method of claim 10, wherein the functional assay is a kinase assay.

15. A method of diagnosing, theranosing, prognosing, or determining treatment efficacy for a subject suffering from a synucleopathy involving Lewy body neurodegeneration, comprising
   a. obtaining a biological sample from said subject;
   b. contacting said biological sample with a phosphorylation site-specific antibody that specifically binds LRRK2 only when the LRRK2 is phosphorylated at Ser955; and
   c. detecting binding of said phosphorylation site-specific antibody to LRRK2, thereby diagnosing, theranosing, prognosing, or determining treatment efficacy for said subject.

16. The method of claim 15, wherein the synucleopathy involving Lewy body neurodegeneration is Parkinson's Disease.

17. A kit useful for performing the method of claim 2 or 15, said kit comprising an isolated phosphorylation site-specific antibody that specifically binds LRRK2 when phosphorylated at Ser955.

* * * * *